United States Patent
Thierry et al.

(10) Patent No.: US 10,704,104 B2
(45) Date of Patent: Jul. 7, 2020

(54) METHODS FOR SCREENING A SUBJECT FOR A CANCER

(71) Applicants: INSERM (INSTITUT NATIONAL DE LA SANTÉ ET DE LA RECHERCHE MÉDICALE), Paris (FR); INSTITUT REGIONAL DU CANCER DE MONTPELLIER, Montpellier (FR); UNIVERSITE DE MONTPELLIER, Montpellier (FR)

(72) Inventors: Alain Thierry, Montpellier (FR); Safia El Messaoudi, Montepplier (FR)

(73) Assignees: INSERM (INSTITUT NATIONAL DE LA SANTE ET DE LA RECHERCHE MEDICALE), Paris (FR); INSTITUT REGIONAL DU CANCER DE MONTPELLIER, Montpellier (FR); UNIVERSITE DE MONTPELLIER, Montpellier (FR)

( * ) Notice: Subject to any disclaimer, the term of this patent is extended or adjusted under 35 U.S.C. 154(b) by 369 days.

(21) Appl. No.: 15/518,392

(22) PCT Filed: Oct. 20, 2015

(86) PCT No.: PCT/IB2015/002046
§ 371 (c)(1),
(2) Date: Apr. 11, 2017

(87) PCT Pub. No.: WO2016/063122
PCT Pub. Date: Apr. 28, 2016

(65) Prior Publication Data
US 2017/0240975 A1    Aug. 24, 2017

(30) Foreign Application Priority Data

Oct. 20, 2014  (EP) ..................................... 14306666

(51) Int. Cl.
*C12Q 1/6886*  (2018.01)
*G01N 33/50*  (2006.01)

(52) U.S. Cl.
CPC ...... *C12Q 1/6886* (2013.01); *C12Q 2600/112* (2013.01); *C12Q 2600/118* (2013.01); *C12Q 2600/158* (2013.01)

(58) Field of Classification Search
CPC ....................... C12Q 1/6886; C12Q 2600/158
See application file for complete search history.

(56) References Cited

FOREIGN PATENT DOCUMENTS

WO    2012/097849 A2    7/2012

OTHER PUBLICATIONS

Bronkhorst, A.J. et al., The emerging role of cell-free DNA as a molecular marker for cancer management, Biomol. Detect. Quantit., vol. 17, 10087, pp. 1-23 (Year: 2019).*

(Continued)

*Primary Examiner* — Teresa E Strzelecka
(74) *Attorney, Agent, or Firm* — W&C IP

(57) ABSTRACT

The present invention relates to methods for screening a subject for a cancer. In particular, the present invention relates to a method (A) for screening a subject for a cancer comprising the steps of i) extracting the cell free nucleic acids from a sample obtained from the subject, ii) determining the total concentration of mitochondrial cell free nucleic acids, ii) determining the total concentration of nuclear cell free nucleic acids iv) calculating the ratio of the level determined at step ii) to the concentration determined at step iii), v) comparing ratio determined at step iv) with a predetermined corresponding reference value and vi) concluding that the subject suffers from a cancer when the ratio determined at step iv) is lower than the predetermined corresponding reference value or concluding that the subject does not suffer from a cancer when the ratio determined at step iv)

(Continued)

is higher than the predetermined corresponding reference value.

16 Claims, 15 Drawing Sheets

Specification includes a Sequence Listing.

(56) References Cited

OTHER PUBLICATIONS

Meddeb, R. et al., Quantifying circulating cell-free DNA in humans, Scientific Reports, vol. 9: 5220, pp. 1-16 (Year: 2019).*

Kohler et al., "Levels of plasma circulating cell free nuclear and mitochondrial DNA as potential biomarkers for breast tumors", Molecular Cancer, Nov. 17, 2009, p. 105, vol. 8, No. 1, Biomed Central, London.

Ellinger et al., "Circulating mitochondrial DNA in serum: A universal diagnostic biomarker for patients with urological malignancies", Urologic Oncology: Seminars and Original Investigations, Jul. 1, 2012, pp. 509-515, vol. 30, No. 4.

Uzawa et al., "Circulating tumor-derived mutant mitochondrial DNA: a predictive biomarker of clinical prognosis in human squamous cell carcinoma", Oncotarget, Jul. 1, 2012, pp. 670-677, Web.

\* cited by examiner

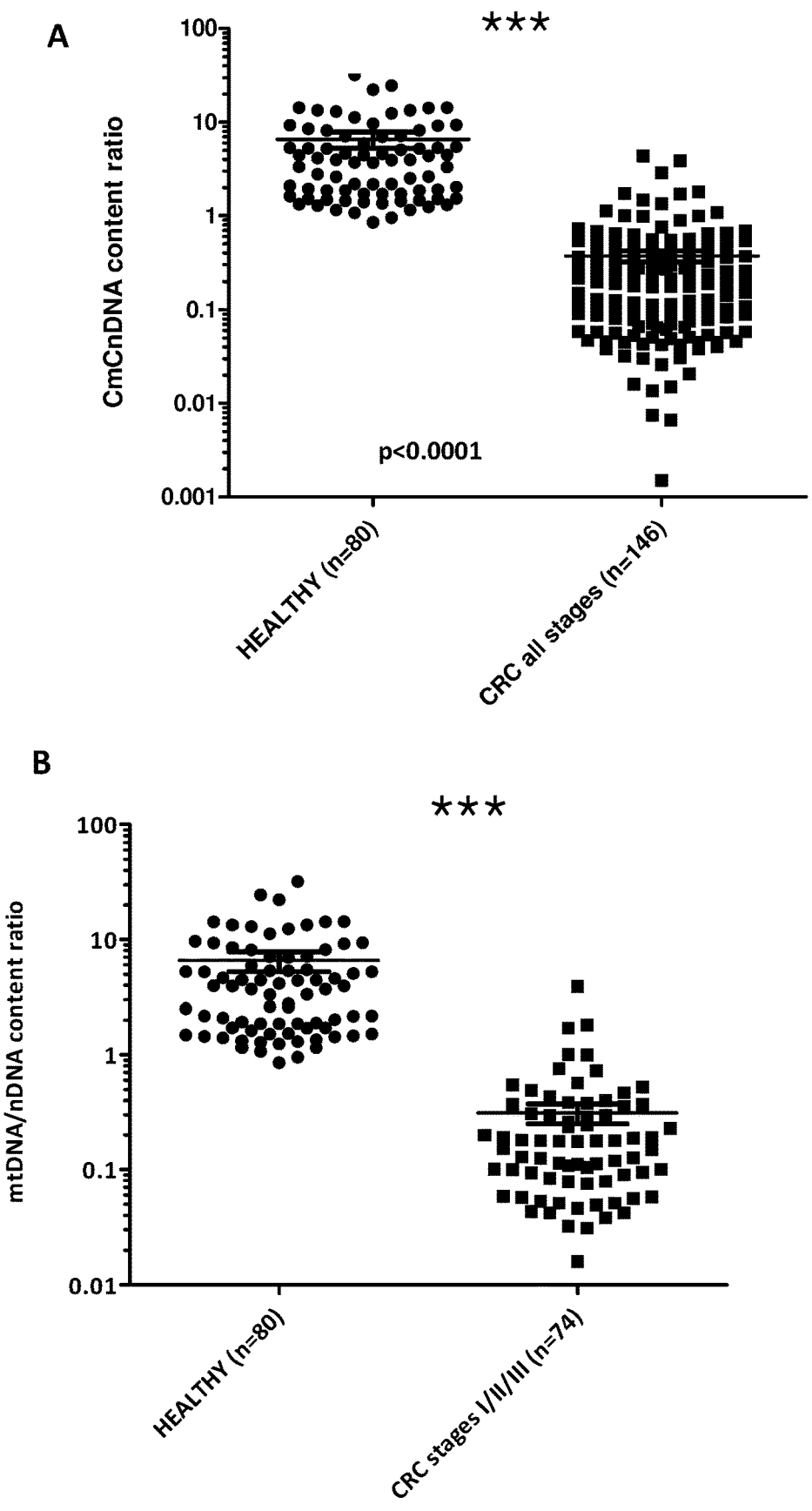
Figure 2 A and B

Figure 3C:
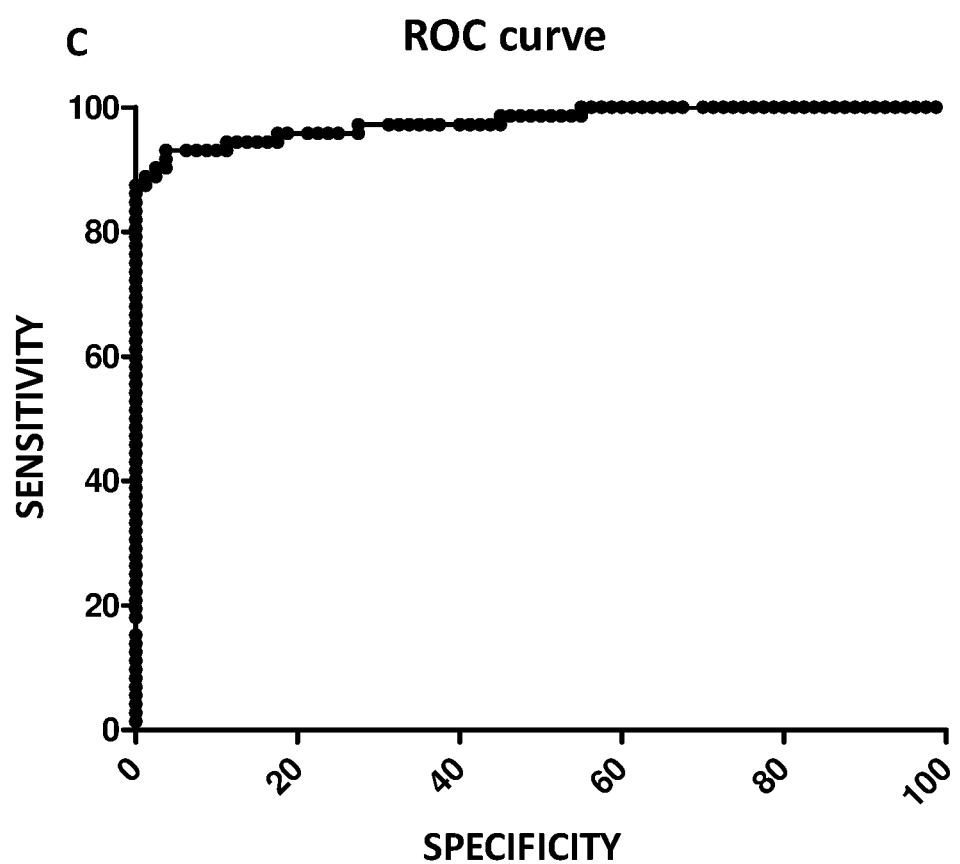

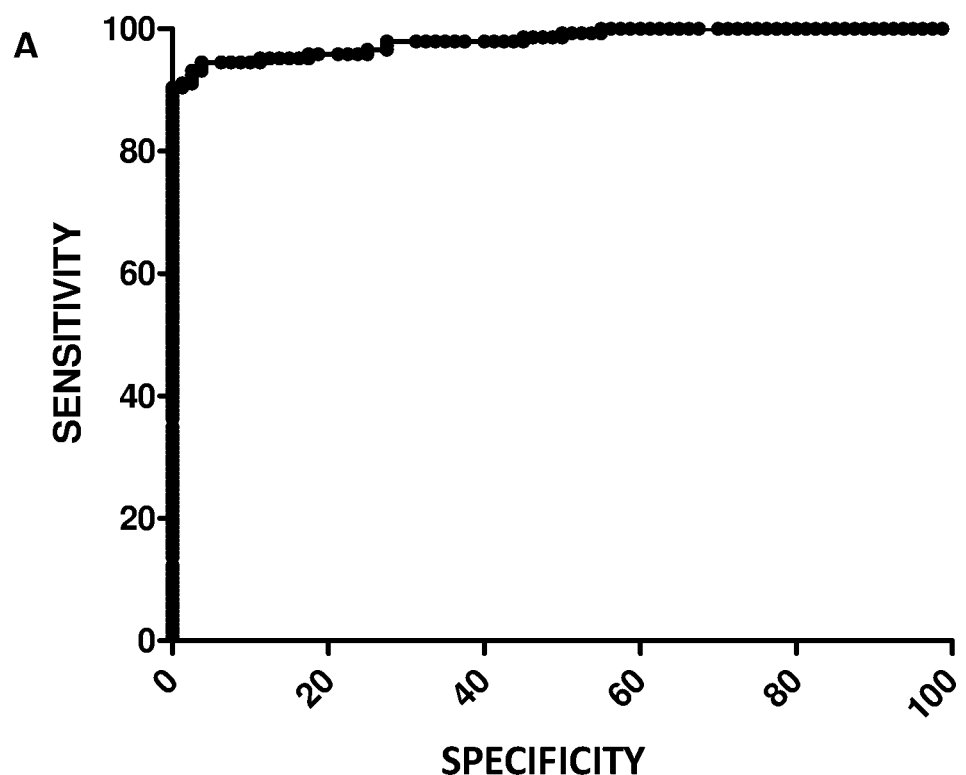
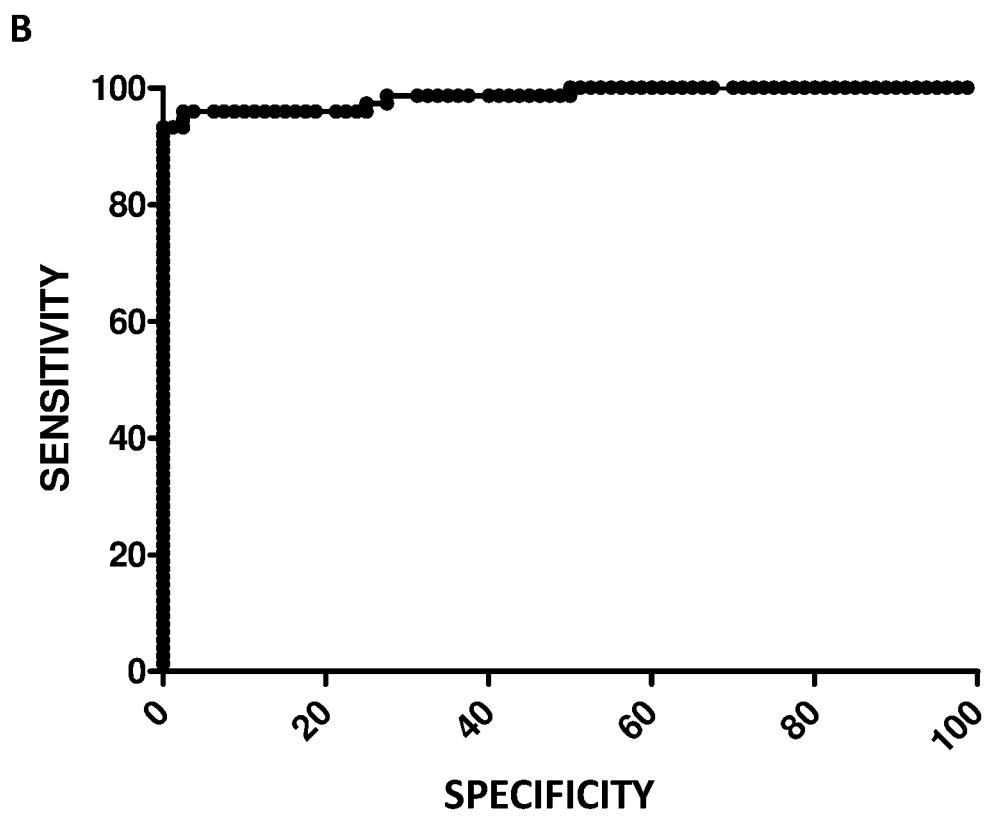
Figure 3 A and B

Nuclear DNA target sequence (KRAS)

Mitochondrial DNA target sequence (mt Co1, cytochrome C oxydase 1)

SEQUENCE LISTING

<160> NUMBER OF SEQ ID NOS: 13

<210> SEQ ID NO 1
<211> LENGTH: 16569
<212> TYPE: DNA
<213> ORGANISM: Homo sapiens
<220> FEATURE:
<221> NAME/KEY: misc_feature
<222> LOCATION: (3107)..(3107)
<223> OTHER INFORMATION: n is a, c, g, or t

<400> SEQUENCE: 1

```
gatcacaggt ctatcaccct attaaccact cacgggagct ctccatgcat ttggtatttt      60
cgtctggggg gtatgcacgc gatagcattg cgagacgctg gagccggagc accctatgtc     120
gcagtatctg tctttgattc ctgcctcatc ctattattta tcgcacctac gttcaatatt     180
acaggcgaac atacttacta aagtgtgtta attaattaat gcttgtagga cataataata     240
acaattgaat gtctgcacag ccactttcca cacagacatc ataacaaaaa atttccacca     300
aaccccccct ccccgcttc tggccacagc acttaaacac atctctgcca aaccccaaaa     360
acaaagaacc ctaacaccag cctaaccaga tttcaaattt tatctttttgg cggtatgcac     420 ttttaacagt cacccccaa ctaacacatt attttcccct cccactccca tactactaat     480
ctcatcaata caaccccgc ccatcctacc cagcacacac acaccgctgc taacccata     540 ccccgaacca accaaacccc aaagacaccc cccacagttt atgtagctta cctcctcaaa     600
gcaatacact gaaaatgttt agacgggctc acatcacccc ataaacaaat aggtttggtc     660
ctagcctttc tattagctct tagtaagatt acacatgcaa gcatcccgt tccagtgagt     720 tcaccctcta aatcaccacg atcaaaagga acaagcatca agcacgcagc aatgcagctc     780
aaaacgctta gcctagccac accccacgg gaaacagcag tgattaacct ttagcaataa     840
acgaaagttt aactaagcta tactaacccc agggttggtc aatttcgtgc cagccaccgc     900
```

```
ggtcacacga ttaacccaag tcaatagaag ccggcgtaaa gagtgtttta gatcaccccc      960
tccccaataa agctaaaact cacctgagtt gtaaaaaact ccagttgaca caaaatagac     1020
tacgaaagtg gctttaacat atctgaacac acaatagcta agacccaaac tgggattaga     1080
taccccacta tgcttagccc taaacctcaa cagttaaatc aacaaaactg ctcgccagaa     1140
cactacgagc cacagcttaa aactcaaagg acctggcggt gcttcatatc cctctagagg     1200
agcctgttct gtaatcgata aaccccgatc aacctcacca cctcttgctc agcctatata     1260
ccgccatctt cagcaaaccc tgatgaaggc tacaaagtaa gcgcaagtac ccacgtaaag     1320
acgttaggtc aaggtgtagc ccatgaggtg gcaagaaatg ggctacattt tctaccccag     1380
aaaactacga tagcccttat gaaacttaag ggtcgaaggt ggatttagca gtaaactaag     1440
agtagagtgc ttagttgaac agggccctga agcgcgtaca caccgcccgt caccctcctc     1500
aagtatactt caaaggacat ttaactaaaa cccctacgca tttatataga ggagacaagt     1560
cgtaacatgg taagtgtact ggaaagtgca cttggacgaa ccagagtgta gcttaacaca     1620
aagcacccaa cttacactta ggagatttca acttaacttg accgctctga gctaaaccta     1680
gccccaaacc cactccacct tactaccaga caaccttagc caaaccattt acccaaataa     1740
agtataggcg atagaaattg aaacctggcg caatagatat agtaccgcaa gggaaagatg     1800
aaaaattata accaagcata atatagcaag gactaacccc tataccttct gcataatgaa     1860
ttaactagaa ataactttgc aaggagagcc aaagctaaga cccccgaaac cagacgagct     1920
acctaagaac agctaaaaga gcacaccccgt ctatgtagca aaatagtggg aagatttata     1980
ggtagaggcg acaaacctac cgagcctggt gatagctggt tgtccaagat agaatcttag     2040
ttcaacttta aatttgccca cagaaccctc taaatcccct tgtaaattta actgttagtc     2100
caaagaggaa cagctctttg gacactagga aaaaccttg tagagagagt aaaaaattta     2160
acacccatag taggcctaaa agcagccacc aattaagaaa gcgttcaagc tcaacaccca     2220
ctacctaaaa aatcccaaac atataactga actcctcaca cccaattgga ccaatctatc     2280
accctataga agaactaatg ttagtataag taacatgaaa acattctcct ccgcataagc     2340
ctgcgtcaga ttaaaacact gaactgacaa ttaacagccc aatatctaca atcaaccaac     2400
aagtcattat taccctcact gtcaacccaa cacaggcatg ctcataagga aaggttaaaa     2460
aaagtaaaag gaactcggca atcttaccc cgcctgttta ccaaaaacat cacctctagc     2520
atcaccagta ttagaggcac cgcctgccca gtgacacatg tttaacggcc gcggtaccct     2580
aaccgtgcaa aggtagcata atcacttgtt ccttaaatag ggacctgtat gaatggctcc     2640
acgagggttc agctgtctct tacttttaac cagtgaaatt gacctgcccg tgaagaggcg     2700
ggcataacac agcaagacga gaagacccta tggagcttta atttattaat gcaaacagta     2760
cctaacaaac ccacaggtcc taaactacca aacctgcatt aaaaatttcg gttggggcga     2820
cctcggagca gaacccaacc tccgagcagt acatgctaag acttcaccag tcaaagcgaa     2880
ctactatact caattgatcc aataacttga ccaacggaac aagttaccct agggataaca     2940
gcgcaatcct attctagagt ccatatcaac aatagggttt acgacctcga tgttggatca     3000
ggacatcccg atggtgcagc cgctattaaa ggttcgtttg ttcaacgatt aaagtcctac     3060
gtgatctgag ttcagaccgg agtaatccag gtcggtttct atctacnttc aaattcctcc     3120
ctgtacgaaa ggacaagaga ataaggcct acttcacaaa gcgccttccc ccgtaaatga     3180
tatcatctca acttagtatt ataccccacac ccacccaaga cagggtttg ttaagatggc     3240 agagcccggt aatcgcataa aacttaaaac tttacagtca gaggttcaat tcctcttctt     3300
```

```
aacaacatac ccatggccaa cctcctactc ctcattgtac ccattctaat cgcaatggca    3360
ttcctaatgc ttaccgaacg aaaaattcta ggctatatac aactacgcaa aggccccaac    3420
gttgtaggcc cctacgggct actacaaccc ttcgctgacg ccataaaact cttcaccaaa    3480
gagcccctaa aacccgccac atctaccatc accctctaca tcaccgcccc gaccttagct    3540
ctcaccatcg ctcttctact atgaaccccc ctccccatac caacccccct ggtcaacctc    3600
aacctaggcc tcctatttat tctagccacc tctagcctag ccgtttactc aatcctctga    3660
tcagggtgag catcaaactc aaactacgcc ctgatcggcg cactgcgagc agtagcccaa    3720
acaatctcat atgaagtcac cctagccatc attctactat caacattact aataagtggc    3780
tcctttaacc tctccaccct tatcacaaca caagaacacc tctgattact cctgccatca    3840
tgacccttgg ccataatatg atttatctcc acactagcag agaccaaccg aaccccttc    3900 gaccttgccg aaggggagtc cgaactagtc tcaggcttca acatcgaata cgccgcaggc    3960
cccttcgccc tattcttcat agccgaatac acaaacatta ttataataaa cacccctcacc   4020 actacaatct tcctaggaac aacatatgac gcactctccc ctgaactcta cacaacatat    4080
tttgtcacca agaccctact tctaacctcc ctgttcttat gaattcgaac agcataccccc   4140 cgattccgct acgaccaact catacacctc ctatgaaaaa acttcctacc actcaccta    4200 gcattactta tatgatatgt ctccataccc attacaatct ccagcattcc ccctcaaacc    4260
taagaaatat gtctgataaa agagttactt tgatagagta aataatagga gcttaaaccc    4320
ccttatttct aggactatga gaatcgaacc catccctgag aatccaaaat tctccgtgcc    4380
acctatcaca ccccatccta agtaaggtc agctaaataa gctatcgggc ccatacccccg   4440 aaaatgttgg ttatacccctt cccgtactaa ttaatcccct ggcccaaccc gtcatctact    4500
ctaccatctt tgcaggcaca ctcatcacag cgctaagctc gcactgattt tttacctgag    4560
taggcctaga aataaacatg ctagcttta ttccagttct aaccaaaaaa ataaaccctc     4620
gttccacaga agctgccatc aagtatttcc tcacgcaagc aaccgcatcc ataatccttc    4680
taatagctat cctcttcaac aatatactct ccggacaatg aaccataacc aatactacca    4740
atcaatactc atcattaata atcataatag ctatagcaat aaaactagga atagccccct    4800
ttcacttctg agtcccagag gttacccaag gcacccctct gacatccggc ctgcttcttc    4860
tcacatgaca aaaactagcc cccatctcaa tcatatacca aatctctccc tcactaaacg    4920
taagccttct cctcactctc tcaatcttat ccatcatagc aggcagttga ggtggattaa    4980
accaaaccca gctacgcaaa atcttagcat actcctcaat tacccacata ggatgaataa    5040
tagcagttct accgtacaac cctaacataa ccattcttaa tttaactatt tatattatcc    5100
taactactac cgcattccta ctactcaact taaactccag caccacgacc ctactactat    5160
ctcgcacctg aaacaagcta acatgactaa cacccttaat tccatccacc ctcctctccc    5220
taggaggcct gccccccgcta accggctttt tgcccaaatg gccattatc gaagaattca    5280 caaaaaacaa tagcctcatc atccccacca tcatagccac catcaccctc cttaacctct    5340
acttctacct acgcctaatc tactccacct caatcacact actccccata tctaacaacg    5400
taaaaataaa atgacagttt gaacatacaa aaccccacccc attcctcccc acactcatcg    5460
cccttaccac gctactccta cctatctccc cttttatact aataatctta tagaaattta    5520
ggttaaatac agaccaagag ccttcaaagc cctcagtaag ttgcaatact taatttctgt    5580
aacagctaag gactgcaaaa ccccactctg catcaactga acgcaaatca gccactttaa    5640
```

-continued

| | | | | |
|---|---|---|---|---|
| ttaagctaag | cccttactag | accaatggga | cttaaaccca | caaacactta gttaacagct | 5700 |
| aagcacccta | atcaactggc | ttcaatctac | ttctcccgcc | gccgggaaaa aaggcgggag | 5760 |
| aagccccggc | aggtttgaag | ctgcttcttc | gaatttgcaa | ttcaatatga aaatcacctc | 5820 |
| ggagctggta | aaaagaggcc | taaccctgt | ctttagattt | acagtccaat gcttcactca | 5880 |
| gccattttac | ctcacccca | ctgatgttcg | ccgaccgttg | actattctct acaaaccaca | 5940 |
| aagacattgg | aacactatac | ctattattcg | gcgcatgagc | tggagtccta ggcacagctc | 6000 |
| taagcctcct | tattcgagcc | gagctgggcc | agccaggcaa | ccttctaggt aacgaccaca | 6060 |
| tctacaacgt | tatcgtcaca | gcccatgcat | ttgtaataat | cttcttcata gtaataccca | 6120 |
| tcataatcgg | aggctttggc | aactgactag | ttcccctaat | aatcggtgcc cccgatatgg | 6180 |
| cgtttccccg | cataaacaac | ataagcttct | gactcttacc | tccctctctc ctactcctgc | 6240 |
| tcgcatctgc | tatagtggag | gccggagcag | gaacaggttg | aacagtctac cctcccttag | 6300 |
| cagggaacta | ctcccaccct | ggagcctccg | tagacctaac | catcttctcc ttacacctag | 6360 |
| caggtgtctc | ctctatctta | ggggccatca | atttcatcac | aacaattatc aatataaaac | 6420 |
| cccctgccat | aacccaatac | caaacgcccc | tcttcgtctg | atccgtccta atcacagcag | 6480 |
| tcctacttct | cctatctctc | ccagtcctag | ctgctggcat | cactatacta ctaacagacc | 6540 |
| gcaacctcaa | caccaccttc | ttcgaccccg | ccggaggagg | agaccccatt ctataccaac | 6600 |
| acctattctg | attttcggt | caccctgaag | tttatattct | tatcctacca ggcttcggaa | 6660 |
| taatctccca | tattgtaact | tactactccg | gaaaaaaga | accatttgga tacataggta | 6720 |
| tggtctgagc | tatgatatca | attggcttcc | tagggtttat | cgtgtgagca caccatatat | 6780 |
| ttacagtagg | aatagacgta | gacacacgag | catatttcac | ctccgctacc ataatcatcg | 6840 |
| ctatccccac | cggcgtcaaa | gtatttagct | gactcgccac | actccacgga agcaatatga | 6900 |
| aatgatctgc | tgcagtgctc | tgagccctag | gattcatctt | tcttttcacc gtaggtggcc | 6960 |
| tgactggcat | tgtattagca | aactcatcac | tagacatcgt | actacacgac acgtactacg | 7020 |
| ttgtagccca | cttccactat | gtcctatcaa | taggagctgt | atttgccatc ataggaggct | 7080 |
| tcattcactg | atttcccta | ttctcaggct | acaccctaga | ccaaacctac gccaaaatcc | 7140 |
| atttcactat | catattcatc | ggcgtaaatc | taactttctt | cccacaacac tttctcggcc | 7200 |
| tatccggaat | gccccgacgt | tactcggact | accccgatgc | atacaccaca tgaaacatcc | 7260 |
| tatcatctgt | aggctcattc | atttctctaa | cagcagtaat | attaataatt ttcatgattt | 7320 |
| gagaagcctt | cgcttcgaag | cgaaaagtcc | taatagtaga | agaaccctcc ataaacctgg | 7380 |
| agtgactata | tggatgcccc | ccaccctacc | acacattcga | agaacccgta tacataaaat | 7440 |
| ctagacaaaa | aaggaaggaa | tcgaaccccc | caaagctggt | ttcaagccaa ccccatggcc | 7500 |
| tccatgactt | tttcaaaaag | gtattagaaa | aaccatttca | taactttgtc aaagttaaat | 7560 |
| tataggctaa | atcctatata | tcttaatggc | acatgcagcg | caagtaggtc tacaagacgc | 7620 |
| tacttcccct | atcatagaag | agcttatcac | ctttcatgat | cacgccctca taatcatttt | 7680 |
| ccttatctgc | ttcctagtcc | tgtatgccct | tttcctaaca | ctcacaacaa aactaactaa | 7740 |
| tactaacatc | tcagacgctc | aggaaataga | aaccgtctga | actatcctgc ccgccatcat | 7800 |
| cctagtcctc | atcgccctcc | catccctacg | catccttac | ataacagacg aggtcaacga | 7860 |
| tccctccctt | accatcaaat | caattggcca | ccaatggtac | tgaacctacg agtacaccga | 7920 |
| ctacggcgga | ctaatcttca | actcctacat | acttccccca | ttattcctag aaccaggcga | 7980 |
| cctgcgactc | cttgacgttg | acaatcgagt | agtactcccg | attgaagccc ccattcgtat | 8040 |

```
aataattaca tcacaagacg tcttgcactc atgagctgtc cccacattag gcttaaaaac    8100
agatgcaatt cccggacgtc taaaccaaac cactttcacc gctacacgac cgggggtata    8160
ctacggtcaa tgctctgaaa tctgtggagc aaaccacagt ttcatgccca tcgtcctaga    8220
attaattccc ctaaaaatct ttgaaatagg gcccgtattt accctatagc accccctcta    8280 cccctctag agcccactgt aaagctaact tagcattaac cttttaagtt aaagattaag     8340
agaaccaaca cctctttaca gtgaaatgcc ccaactaaat actaccgtat ggcccaccat    8400
aattaccccc atactcctta cactattcct catcacccaa ctaaaaatat aaacacaaa     8460 ctaccaccta cctccctcac caaagcccat aaaaataaaa aattataaca aaccctgaga    8520
accaaaatga acgaaaatct gttcgcttca ttcattgccc ccacaatcct aggcctaccc    8580
gccgcagtac tgatcattct atttccccct ctattgatcc ccacctccaa atatctcatc    8640
aacaaccgac taatcaccac ccaacaatga ctaatcaaac taacctcaaa acaaatgata    8700
accatacaca cactaaagg acgaacctga tctcttatac tagtatccctt aatcattttt    8760 attgccacaa ctaacctcct cggactcctg cctcactcat ttacaccaac cacccaacta    8820
tctataaacc tagccatggc catccccta tgagcgggca cagtgattat aggctttcgc    8880
tctaagatta aaaatgccct agcccacttc ttaccacaag gcacacctac accccttatc    8940
cccatactag ttattatcga aaccatcagc ctactcattc aaccaatagc cctggccgta    9000
cgcctaaccg ctaacattac tgcaggccac ctactcatgc acctaattgg aagcgccacc    9060
ctagcaatat caaccattaa ccttccctct acacttatca tcttcacaat tctaattcta    9120
ctgactatcc tagaaatcgc tgtcgcctta atccaagcct acgttttcac acttctagta    9180
agcctctacc tgcacgacaa cacataatga cccaccaatc acatgcctat catatagtaa    9240
aacccagccc atgaccccta cagggggccc tctcagccct cctaatgacc tccggcctag    9300
ccatgtgatt tcacttccac tccataacgc tcctcatact aggcctacta accaacacac    9360
taaccatata ccaatgatgg cgcgatgtaa cacgagaaag cacataccaa ggccaccaca    9420
caccacctgt ccaaaaaggc cttcgatacg ggataatcct atttattacc tcagaagttt    9480
ttttcttcgc aggattttc tgagcctttt accactccag cctagcccct accccccaat     9540
taggagggca ctggcccca acaggcatca ccccgctaaa tccctagaa gtcccactcc      9600 taaacacatc cgtattactc gcatcaggag tatcaatcac ctgagctcac catagtctaa    9660
tagaaaacaa ccgaaaccaa ataattcaag cactgcttat tacaatttta ctgggtctct    9720 attttacccct cctacaagcc tcagagtact tcgagtctcc cttcaccatt tccgacggca    9780
tctacggctc aacatttttt gtagccacag gcttccacgg acttcacgtc attattggct    9840
caactttcct cactatctgc ttcatccgcc aactaatatt tcactttaca tccaaacatc    9900
actttggctt cgaagccgcc gcctgatact ggcattttgt agatgtggtt tgactatttc    9960
tgtatgtctc catctattga tgagggtctt actcttttag tataaatagt accgttaact    10020
tccaattaac tagttttgac aacattcaaa aaagagtaat aaacttcgcc ttaattttaa    10080
taatcaacac cctcctagcc ttactactaa taattattac attttgacta ccacaactca    10140
acggctacat agaaaaatcc accccttacg agtgcggctt cgaccctata tcccccgccc    10200
gcgtcccttt ctccataaaa ttcttcttag tagctattac cttcttatta tttgatctag    10260
aaattgccct ccttttaccc ctaccatgag ccctacaaac aactaacctg ccactaatag    10320
ttatgtcatc cctcttatta atcatcatcc tagccctaag tctggcctat gagtgactac    10380
```

```
aaaaaggatt agactgaacc gaattggtat atagtttaaa caaaacgaat gatttcgact    10440
cattaaatta tgataatcat atttaccaaa tgcccctcat ttacataaat attatactag    10500
catttaccat ctcacttcta ggaatactag tatatcgctc acacctcata tcctccctac    10560
tatgcctaga aggaataata ctatcgctgt tcattatagc tactctcata accctcaaca    10620
cccactccct cttagccaat attgtgccta ttgccatact agtctttgcc gcctgcgaag    10680
cagcggtggg cctagcccta ctagtctcaa tctccaacac atatggccta gactacgtac    10740
ataacctaaa cctactccaa tgctaaaact aatcgtccca acaattatat tactaccact    10800
gacatgactt tccaaaaaac acataatttg aatcaacaca accacccaca gcctaattat    10860
tagcatcatc cctctactat ttttaacca aatcaacaac aacctattta gctgttcccc    10920
aaccttttcc tccgaccccc taacaacccc cctcctaata ctaactacct gactcctacc    10980
cctcacaatc atggcaagcc aacgccactt atccagtgaa ccactatcac gaaaaaaact    11040
ctacctctct atactaatct ccctacaaat ctccttaatt ataacattca cagccacaga    11100
actaatcata ttttatatct tcttcgaaac cacacttatc cccaccttgg ctatcatcac    11160
ccgatgaggc aaccagccag aacgcctgaa cgcaggcaca tacttcctat tctacaccct    11220
agtaggctcc cttcccctac tcatcgcact aatttacact cacaacaccc taggctcact    11280
aaacattcta ctactcactc tcactgccca agaactatca aactcctgag ccaacaactt    11340
aatatgacta gcttacacaa tagctttat agtaaagata cctctttacg gactccactt    11400
atgactccct aaagcccatg tcgaagcccc catcgctggg tcaatagtac ttgccgcagt    11460
actcttaaaa ctaggcggct atggtataat acgcctcaca ctcattctca ccccctgac    11520 aaaacacata gcctacccct tccttgtact atccctatga ggcataatta taacaagctc    11580
catctgccta cgacaaacag acctaaaatc gctcattgca tactcttcaa tcagccacat    11640
agccctcgta gtaacagcca ttctcatcca aacccctga agcttcaccg gcgcagtcat    11700
tctcataatc gcccacgggc ttacatcctc attactattc tgcctagcaa actcaaacta    11760
cgaacgcact cacagtcgca tcataatcct ctctcaagga cttcaaactc tactcccact    11820 aatagcttt tgatgacttc tagcaagcct cgctaacctc gccttacccc ccactattaa    11880
cctactggga gaactctctg tgctagtaac cacgttctcc tgatcaaata tcactctcct    11940
acttacagga ctcaacatac tagtcacagc cctatactcc ctctacatat ttaccacaac    12000
acaatggggc tcactcaccc accacattaa caacataaaa ccctcattca cacgagaaaa    12060
caccctcatg ttcatacacc tatcccccat tctcctccta tccctcaacc ccgacatcat    12120
taccgggttt tcctcttgta aatatagttt aaccaaaaca tcagattgtg aatctgacaa    12180
cagaggctta cgaccccta tttaccgaga aagctcacaa gaactgctaa ctcatgcccc    12240
catgtctaac aacatggctt tctcaacttt taaaggataa cagctatcca ttggtcttag    12300
gccccaaaaa ttttggtgca actccaaata aaagtaataa ccatgcacac tactataacc    12360
accctaaccc tgacttccct aattccccc atccttacca ccctcgttaa ccctaacaaa    12420
aaaaactcat accccattta tgtaaaatcc attgtcgcat ccacctttat tatcagtctc    12480
ttccccacaa caatattcat gtgcctagac caagaagtta ttatctcgaa ctgacactga    12540
gccacaaccc aaacaaccca gctctcccta agcttcaaac tagactactt ctccataata    12600
ttcatccctg tagcattgtt cgttacatgg tccatcatag aattctcact gtgatatata    12660
aactcagacc caaacattaa tcagttcttc aaatatctac tcatcttcct aattaccata    12720
ctaatcttag ttaccgctaa caacctattc caactgttca tcggctgaga gggcgtagga    12780
```

```
attatatcct tcttgctcat cagttgatga tacgcccgag cagatgccaa cacagcagcc    12840
attcaagcaa tcctatacaa ccgtatcggc gatatcggtt tcatcctcgc cttagcatga    12900
tttatcctac actccaactc atgagaccca caacaaatag cccttctaaa cgctaatcca    12960
agcctcaccc cactactagg cctcctccta gcagcagcag gcaaatcagc ccaattaggt    13020
ctccacccct gactcccctc agccatagaa ggccccaccc cagtctcagc cctactccac    13080
tcaagcacta tagttgtagc aggaatcttc ttactcatcc gcttccaccc cctagcagaa    13140
aatagcccac taatccaaac tctaacacta tgcttaggcg ctatcaccac tctgttcgca    13200
gcagtctgcg cccttacaca aaatgacatc aaaaaaatcg tagccttctc cacttcaagt    13260
caactaggac tcataatagt tacaatcggc atcaaccaac cacacctagc attcctgcac    13320
atctgtaccc acgccttctt caaagccata ctatttatgt gctccgggtc catcatccac    13380
aaccttaaca atgaacaaga tattcgaaaa ataggaggac tactcaaaac catacctctc    13440
acttcaacct ccctcaccat tggcagccta gcattagcag gaatacccttt cctcacaggt    13500 ttctactcca agaccacat catcgaaacc gcaaacatat catacacaaa cgcctgagcc    13560
ctatctatta ctctcatcgc tacctccctg acaagcgcct atagcactcg aataattctt    13620
ctcaccctaa caggtcaacc tcgcttcccc acccttacta acattaacga aaataacccc    13680
accctactaa accccattaa cgcctggca gccggaagcc tattcgcagg atttctcatt    13740
actaacaaca tttccccgc atccccttc caaacaacaa tcccctcta cctaaaactc    13800 acagccctcg ctgtcacttt cctaggactt ctaacagccc tagacctcaa ctacctaacc    13860
aacaaactta aaataaaatc cccactatgc acatttttatt tctccaacat actcggattc    13920 tacccctagca tcacacaccg cacaatcccc tatctaggcc ttcttacgag ccaaaacctg    13980
cccctactcc tcctagacct aacctgacta gaaaagctat acctaaaac aatttcacag    14040 caccaaatct ccacctccat catcacctca acccaaaag gcataattaa actttacttc    14100
ctctctttct tcttcccact catcctaacc ctactcctaa tcacataacc tattccccg    14160 agcaatctca attacaatat atacaccaac aaacaatgtt caaccagtaa ctactactaa    14220
tcaacgccca taatcataca agccccgc accaatagga tcctcccgaa tcaaccctga    14280
cccctctcct tcataaaatta ttcagcttcc tacactatta agtttaccaa caaccaccac    14340
cccatcatac tcttcacccc acagcaccaa tcctacctcc atcgctaacc ccactaaaac    14400
actcaccaag acctcaaccc ctgaccccca tgcctcagga tactcctcaa tagccatcgc    14460
tgtagtatat ccaaagacaa ccatcattcc ccctaataa attaaaaaaa ctattaaacc    14520 catataaccct cccccaaaat tcagaataat aacacacccg accacaccgc taacaatcaa    14580
tactaaaccc ccataaatag gagaaggctt agaagaaaac cccacaaacc ccattactaa    14640
acccacactc aacagaaaca agcatacat cattattctc gcacggacta caaccacgac    14700
caatgatatg aaaaaccatc gttgtatttc aactacaaga acaccaatga ccccaatacg    14760
caaaactaac cccctaataa aattaattaa ccactcattc atcgacctcc ccaccccatc    14820
caacatctcc gcatgatgaa acttcggctc actccttggc gcctgcctga tcctccaaat    14880
caccacagga ctattcctag ccatgcacta ctcaccagac gcctcaaccg ccttttcatc    14940
aatcgcccac atcactcgag acgtaaatta tggctgaatc atccgctacc ttcacgccaa    15000
tggcgcctca atattctta tctgcctctt cctacacatc gggcgaggcc tatattacgg    15060
atcatttctc tactcagaaa cctgaaacat cggcattatc ctcctgcttg caactatagc    15120
```

```
aacagccttc ataggctatg tcctcccgtg aggccaaata tcattctgag gggccacagt   15180
aattacaaac ttactatccg ccatcccata cattgggaca gacctagttc aatgaatctg   15240
aggaggctac tcagtagaca gtcccaccct cacacgattc tttacctttc acttcatctt   15300
gcccttcatt attgcagccc tagcaacact ccacctccta ttcttgcacg aaacgggatc   15360
aaacaacccc ctaggaatca cctcccattc cgataaaatc accttccacc cttactacac   15420
aatcaaagac gccctcggct tacttctctt ccttctctcc ttaatgacat taacactatt   15480
ctcaccagac ctcctaggcg acccagacaa ttatacccta gccaacccct aaacacccc    15540 tccccacatc aagcccgaat gatatttcct attcgcctac acaattctcc gatccgtccc   15600
taacaaacta ggaggcgtcc ttgccctatt actatccatc ctcatcctag caataatccc   15660
catcctccat atatccaaac aacaaagcat aatatttcgc ccactaagcc aatcacttta   15720
ttgactccta gccgcagacc tcctcattct aacctgaatc ggaggacaac cagtaagcta   15780
cccttttacc atcattggac aagtagcatc cgtactatac ttcacaacaa tcctaatcct   15840
aataccaact atctccctaa ttgaaaacaa aatactcaaa tgggcctgtc cttgtagtat   15900
aaactaatac accagtcttg taaaccggag atgaaaacct ttttccaagg acaaatcaga   15960
gaaaaagtct ttaactccac cattagcacc caaagctaag attctaattt aaactattct   16020
ctgttctttc atggggaagc agatttgggt accacccaag tattgactca cccatcaaca   16080
accgctatgt atttcgtaca ttactgccag ccaccatgaa tattgtacgg taccataaat   16140
acttgaccac ctgtagtaca taaaaaccca atccacatca aaacccctc cccatgctta    16200 caagcaagta cagcaatcaa ccctcaacta tcacacatca actgcaactc caaagccacc   16260
cctcacccac taggatacca acaaacctac ccacccttaa cagtacatag tacataaagc   16320
catttaccgt acatagcaca ttacagtcaa atcccttctc gtccccatgg atgacccccc   16380
tcagataggg gtcccttgac caccatcctc cgtgaaatca atatcccgca caagagtgct   16440
actctcctcg ctccgggccc ataacacttg ggggtagcta aagtgaactg tatccgacat   16500
ctggttccta cttcagggtc ataaagccta aatagcccac acgttcccct taaataagac   16560
atcacgatg                                                           16569
```

<210> SEQ ID NO 2
<211> LENGTH: 18
<212> TYPE: DNA
<213> ORGANISM: Artificial
<220> FEATURE:
<223> OTHER INFORMATION: Synthetic oligomucleotide primer

<400> SEQUENCE: 2
gacccaccaa tcacatgc                                                 18

<210> SEQ ID NO 3
<211> LENGTH: 18
<212> TYPE: DNA
<213> ORGANISM: Artificial
<220> FEATURE:
<223> OTHER INFORMATION: Synthetic oligomucleotide primer

<400> SEQUENCE: 3
tgagagggcc cctgttag                                                 18

<210> SEQ ID NO 4
<211> LENGTH: 21
<212> TYPE: DNA
<213> ORGANISM: Artificial

```
<220> FEATURE:
<223> OTHER INFORMATION: Synthetic oligomucleotide primer

<400> SEQUENCE: 4
ctcagaaaaa tcctgcgaag a                                              21

<210> SEQ ID NO 5
<211> LENGTH: 19
<212> TYPE: DNA
<213> ORGANISM: Artificial
<220> FEATURE:
<223> OTHER INFORMATION: Synthetic oligomucleotide primer

<400> SEQUENCE: 5
gcctgctgaa aatgactga                                                 19

<210> SEQ ID NO 6
<211> LENGTH: 21
<212> TYPE: DNA
<213> ORGANISM: Artificial
<220> FEATURE:
<223> OTHER INFORMATION: Synthetic oligomucleotide primer

<400> SEQUENCE: 6
ccttgggttt caagttatat g                                              21

<210> SEQ ID NO 7
<211> LENGTH: 20
<212> TYPE: DNA
<213> ORGANISM: Artificial
<220> FEATURE:
<223> OTHER INFORMATION: Synthetic oligomucleotide primer

<400> SEQUENCE: 7
ccctgacata ctcccaagga                                                20

<210> SEQ ID NO 8
<211> LENGTH: 20
<212> TYPE: DNA
<213> ORGANISM: Artificial
<220> FEATURE:
<223> OTHER INFORMATION: Synthetic oligomucleotide primer

<400> SEQUENCE: 8
gtcccactaa taatcggagc                                                20

<210> SEQ ID NO 9
<211> LENGTH: 21
<212> TYPE: DNA
<213> ORGANISM: Artificial
<220> FEATURE:
<223> OTHER INFORMATION: Synthetic oligomucleotide primer

<400> SEQUENCE: 9
tgcttctact attgatgatg c                                              21

<210> SEQ ID NO 10
<211> LENGTH: 20
<212> TYPE: DNA
<213> ORGANISM: Artificial
<220> FEATURE:
<223> OTHER INFORMATION: Synthetic oligomucleotide primer

<400> SEQUENCE: 10
ttgatactgt gttatggctg                                                20
```

```
<210> SEQ ID NO 11
<211> LENGTH: 20
<212> TYPE: DNA
<213> ORGANISM: Artificial
<220> FEATURE:
<223> OTHER INFORMATION: Synthetic oligomucleotide primer

<400> SEQUENCE: 11
aagagtgaag acccgtgtgc                                              20

<210> SEQ ID NO 12
<211> LENGTH: 20
<212> TYPE: DNA
<213> ORGANISM: Artificial
<220> FEATURE:
<223> OTHER INFORMATION: Synthetic oligomucleotide primer

<400> SEQUENCE: 12
ggagaacaag cacccaacag                                              20

<210> SEQ ID NO 13
<211> LENGTH: 23
<212> TYPE: DNA
<213> ORGANISM: Artificial
<220> FEATURE:
<223> OTHER INFORMATION: Synthetic oligomucleotide primer

<400> SEQUENCE: 13
gtctttgtaa ttcccaacct cct                                          23
```

METHODS FOR SCREENING A SUBJECT FOR A CANCER

FIELD OF THE INVENTION

The present invention relates to methods for screening a subject for a cancer.

BACKGROUND OF THE INVENTION

The discovery of circulating cell-free DNA (ccfDNA) in the human circulatory system has led to intensive research on its use in various clinical fields. CcfDNA was discovered in 1948 by Mandel and Metais[1] although at the time, it did not attract much curiosity. Thirty to 40 years later, however, the interest of ccfDNA was demonstrated by several groups: Leon et al.[2] found that ccfDNA concentration was significantly increased in cancer subjects and Stroun et al.[3] described a proportion of ccfDNA that was tumor derived and carried its molecular characteristics, thus leading to the concept of a "liquid biopsy". Additionally, ccfDNA fragmentation has grown in interest in terms of diagnosis since the revelation of significant differences between cancer subjects and healthy subjects[4] (Stroun U.S. Pat. No. 5,952, 170). Therefore, ccfDNA analysis could provide diagnostic, pronostic, and theranostic information[5]. Several researchers are intensively developing techniques that allow detection and characterization of genetic and epigenetic alterations of tumor cells using ccfDNA analysis in the plasma/serum of cancer subjects. Such techniques could revolutionize the management care of cancer subjects through the detection of mutations leading to resistance to targeted therapies, personalized therapeutic monitoring and non-invasive follow-up of the disease. ccfDNA analysis is currently used in prenatal diagnosis practice[6] and a promising analysis in other clinical fields, such as autoimmune diseases, trauma, sepsis, or myocardial infarction[7].

Despite intensive research, few ccfDNA-based tests have been translated to clinical practice. Several techniques are under development to detect and characterize ccfDNA in cancer subjects including restriction fragment length polymorphism, direct sequencing, high-resolution melting analysis, digital PCR, cold PCR, and other techniques usually used for tumor-tissue analysis. Nevertheless, ccfDNA concentration has not yet been validated as a cancer biomarker as the literature reveals conflicting data: plasma ccfDNA concentrations in cancer subjects range from a few ng/ml to several thousand ng/ml, which overlaps with the concentration range for healthy individuals[5]. Furthermore, the estimation of ccfDNA fragmentation in cancer subjects has been found to be lower, equivalent, or higher than in control subjects. These discrepancies may be explained by the lack of fundamental knowledge about ccfDNA. Indeed, the cognitive aspects of ccfDNA are still not identified and elucidated: The respective contributions of different potential release mechanisms of ccfDNA (apoptosis, necrosis, phagocytosis, extracellular DNA traps, active release . . . ) are not clearly identified. Similarly, structures of ccfDNA are not yet clearly defined (part of chromatin, nucleosomes, nucleoprotein complex, exosomes, apoptotic bodies . . . )[8].

Total concentration of circulating DNA was envisaged for long time as a potential biomarker for cancer but cfDNA concentration values from healthy and cancer individuals were partly found overlapping precluding its development as clinical use[9]. With recent methods and specific PCR system design, statistical discrimination was recently showed between healthy subjects and cancer subjects[10]. Moreover, we revealed that circulating tumor DNA is highly fragmented in comparison of cfDNA from healthy subjects (U520130224740,[11]). Targeting short sequences lead to find that up to 50% of total ccfDNA could be derived from the tumor[12] breaking the previous literature statement describing that tumor-derived ccfDNA was a tiny portion of total ccfDNA.

Nevertheless, structural and size characteristics of ccfDNA are still poorly characterized in the literature while it could contribute to improve cognitive knowledge on ccfDNA and to design accurate and specific analytical processes. In addition to the current vigourous research on nuclear ccfDNA (CnDNA) analysis, mitochondrial ccfDNA (CnDNA) analysis is emerging as a very attractive study field.

Mitochondrial DNA (mtDNA) is composed of a circular DNA of 16,000 bp inserting to 37 genes, coding for two rRNAs, 22 tRNAs and 14 polypeptides (above presented, one encoding both ribosomal 16S and humanin). They are 5 to 10 copies of this circular DNA per mitochondria, and exist only in eukaryotes in all types of cells except of red cells; each cells containing 1000 to 3000 mitochondria upon cell types. Thus, there are hundreds to thousands copies of mtDNA, number variation being function upon environmental conditions (such as hypoxia or steroid hormone stimulation)[13]. mtDNA corresponds to about 1% of the total cellular DNA. Since it is derived from bacterial DNA it contains numerous unmethylated CpG dinucleotides[14]. Because of lack of protection by histones and efficient DNA repair mechanisms, it is sensitive to genotoxic and oxidative stress[15]. There is 10 to 200-fold higher mutation rate than nuclear DNA. During tumorogenesis, mitochondrial DNA is subjected to many mutations in much higher proportion than nuclear DNA due to its lack of protection by histones and lack of DNA repair mechanisms. Moreover, this polyploid genome is subjected to copy number variation during carcinogenesis. These specific alterations could be easily determined from mitochondrial ccfDNA since mtDNA copies are present in higher quantity (hundred to thousand copies by cell) than nuclear DNA[13]. Some studies have been published on the clinical significance of mitochondrial ccfDNA concentration and integrity in cancer subjects[16]. At this time, published data are discordant and it is impossible to draw any conclusion. The lack of preanalytical and analytical SOP could explain in part this discordance.

Little is known about the structural properties of mitochondrial ccfDNA (CmDNA). We can hypothesize that they are different of nuclear ccfDNA (CnDNA) since mDNA is not protected by histones and a part of nuclear ccfDNA is made of nucleosomes. It has been shown that Neutrophil released mDNA in a ROS manner dependant to form the Neutrophil Extracellular Traps (NET)[17]. Similarly, Eosinophil release mtDNA to form the extracellular traps (EET) contributing to antibacterial defense[18].

Biologically and physiologically, it has been demonstrated that mitochondrial ccfDNA was a DAMP[14]. Its specific unmethylated CpG pattern and its similar characteristics with bacterial DNA is recognized by TLR9 of immune cells and led to inflammatory response via p38[19]. This point is crucial since little is known about biological properties of ccfDNA and such a discovery could lead to therapeutic agents directed against ccfDNA. For all these reasons, mitochondrial ccfDNA is very promising and further studies on this particular DNA need to be achieved. It

SUMMARY OF THE INVENTION

The present invention relates to methods for screening a subject for a cancer in subject in need thereof. In particular, the present invention is defined by the claims.

DETAILED DESCRIPTION OF THE INVENTION

Here the inventors demonstrate for the first time that quantifying and associating mtDNA and nucDNA content enables to distinguish cancer subject to healthy individuals. More specifically, the mitochondrial ccfDNA/nuclear ccfDNA content ratio (CmCnDNA) is statistically lower in cancer than that of healthy subjects. As diagnosis capacity is optimal (AUC of 1) this value is a strong biomarker to screen for presence of tumor and can be used to screen non-symptomatic or non-diagnosticated individuals. In addition we showed than the fragmentation index (DII as calculated here) of mitochondrial ccfDNA (CmtDNA) is higher than that of nuclear ccfDNA (CnuDNA), the ratio CmtDNA DII/CnuDNA DII being higher in tumor bearing subject than in healthy individuals. Since just the concentration of total nuclear cfDNA (CnDNA) presents a potential for cancer diagnosis, it would be possible to combine CmCnDNA content ratio with either only the concentration of total nuclear cfDNA or both DII ratio and cfDNA concentration of total nuclear cfDNA to improve the screening power especially for large scale screening. An algorithm might be useful towards this goal.

No other biomarker showed up to now such performance as CmCnDNA content ratio to diagnose cancer by a blood test. Numerous attempts were made with either protein or nucleic acids-based biomarkers and all of them were found either non-specific or not-sensitive enough. For instance, PSA is a routinely used biomarker for prostate cancer, but it requires a lot of caution because of non-specific to a malignant disease and of analytical drawbacks in terms of sensitivity. CEA or CA15-3 biomarker is also routinely used in cancer subjects especially for colorectal cancer (CRC) or breast cancer subjects, respectively, but they used only for prognosis, treatment monitoring or surveillance of recurrence.

In addition to its high screening capacity CmCnDNA content ratio may be useful as a biomarker for prognosis, treatment monitoring or surveillance of recurrence in cancer management care.

General Definitions

As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/ squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangio sarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In some embodiments, the subject suffers from a colorectal cancer, more particularly a metastatic colorectal cancer.

As used herein the term "nucleic acid" has its general meaning in the art and refers to refers to a coding or non coding nucleic sequence. Nucleic acids include DNA (deoxyribonucleic acid) and RNA (ribonucleic acid) nucleic acids. Example of nucleic acid thus include but are not limited to DNA, mRNA, tRNA, rRNA, tmRNA, miRNA, piRNA, snoRNA, and snRNA. Nucleic acids thus encompass coding and non coding region of a genome (i.e. nuclear or mitochondrial).

As used herein, the term "nuclear nucleic acid" has its general meaning in the art and refers to a nucleic acid originating from the nucleus of cell. The term nuclear nucleic acid encompasses all forms of the nucleic acids excepting those originating from the mitochondria. The term nuclear nucleic acid is thus defined in opposition to the term "mitochondrial nucleic acid". Mitochondria are indeed structures within cells that convert the energy from food into a form that cells can use. Although most DNA is packaged in chromosomes within the nucleus, mitochondria also have a small amount of their own DNA. This genetic material is known as "mitochondrial DNA" or "mtDNA". In humans, mitochondrial DNA spans about 16,500 DNA building blocks (base pairs), representing a small fraction of the total DNA in cells. Mitochondrial DNA contains 37 genes, all of which are essential for normal mitochondrial function: ATP6; ATP8; COX1; COX2; COX3; CYTB; ND1; ND2; ND3; ND4; ND4L; ND5; ND6; RNR1, RNR2 TRNA; TRNA; TRNC; TRND; TRNE; TRNF; TRNG; TRNI; TRNK; TRNL1; TRNL2; TRNM; TRNN; TRNN; TRNP; TRNQ; TRNR; TRNS1; TRNS2; TRNT; TRNV; TRNW; and TRNY. Genes encoding for NADH dehydrogenase (complex I) include MT-ND1, MT-ND2, MT-ND3, MT-ND4, MT-ND4L, MT-ND5, and MT-ND6. Genes encoding for Coenzyme Q—cytochrome c reductase/Cytochrome b (complex III) include MT-CYB. Gene encoding for cytochrome c oxidase (complex IV) include MT-CO1, MT-CO2, MT-CO3. Gene encoding for ATP synthase (complex V) include MT-ATP6, and MT-ATP8. Gene encoding for humanin include MT-RNR2 (encoding both ribosomal 16S and humanin). MT-RNR1 and MT-RNR2 genes providing instruction to produce ribosomal 12S and 16S respectively. The 22 species of mitochondrial tRNAs (mt tRNAs) encoded by mtDNA involved in mitochondrial protein synthesis machinery. Human mitochondrial DNA (mtDNA) has three promoters, H1, H2, and L (heavy strand 1, heavy strand 2, and light strand promoters). Mitochondrial genome also comprises control regions or d-loop sequences. Mitochondrial nuclear acids are known per se by the skilled person (e.g. NCBI Reference Sequence: NC_012920.1, SEQ ID NO:1). Thirteen of these genes provide instructions for making enzymes involved in oxidative phosphorylation. Oxidative phosphorylation is a process that uses oxygen and simple sugars to create adenosine triphosphate (ATP), the cell's main energy source. The remaining genes provide instructions for making molecules called transfer RNA (tRNA) and ribosomal RNA (rRNA), which are chemical cousins of DNA. These types of RNA help assemble protein building blocks (amino acids) into functioning proteins.

By "cell free nucleic acid" it is meant that the nucleic acid is released by the cell and present in the sample. In some embodiments, the cell free nucleic acid is circulating cell-free DNA (ccfDNA) and it is easy and routine for one of ordinary skill in the art to distinguish mitochondrial ccf nucleic acids" or "mitochondrial ccfDNA" from "nuclear ccfDNA". Actually, mitochondrial ccfDNA encompasses any DNA mitochondrial nucleic acid and in opposition nuclear ccfDNA encompasses any DNA nuclear nucleic acid.

As used herein, the term "target nucleic acid sequence" refers to a specific (coding or non coding) nucleic acid sequence which amplification and quantification is sought by e.g. Q-PCR and/or analyze by. sequencing In particular, a nuclear target nucleic acid sequence is a sequence originating from the human nuclear genome, and a mitochondrial target nucleic acid sequence is a sequence originating from the human mitochondrial genome (e.g. SEQ ID NO:1). According to the invention a target nucleic acid sequence has a length of at 10 base pairs. In particular, a target nucleic acid sequence has a length of 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; or 110; 111; 112; 113; 114; 115; 116; 117; 118; 119; 120; 121; 122; 123; 124; 125; 126; 127; 128; 129; 130; 131; 132; 133; 134; 135; 136; 137; 138; 139; 140; 141; 142; 143; 144; 145; 146; 147; 148; 149; 150; 151; 152; 153; 154; 155; 156; 157; 158; 159; 160; 161; 162; 163; 164; 165; 166; 167; 168; 169; 170; 171; 172; 173; 174; 175; 176; 177; 178; 179; 180; 181; 182; 183; 184; 185; 186; 187; 188; 189; 190; 191; 192; 193; 194; 195; 196; 197; 198; 199; 200; 201; 202; 203; 204; 205; 206; 207; 208; 209; 210; 211; 212; 213; 214; 215; 216; 217; 218; 219; 220; 221; 222; 223; 224; 225; 226; 227; 228; 229; 230; 231; 232; 233; 234; 235; 236; 237; 238; 239; 240; 241; 242; 243; 244; 245; 246; 247; 248; 249; 250; 251; 252; 253; 254; 255; 256; 257; 258; 259; 260; 261; 262; 263; 264; 265; 266; 267; 268; 269; 270; 271; 272; 273; 274; 275; 276; 277; 278; 279; 280; 281; 282; 283; 284; 285; 286; 287; 288; 289; 290; 291; 292; 293; 294; 295; 296; 297; 298; 299; 300; 301; 302; 303; 304; 305; 306; 307; 308; 309; 310; 311; 312; 313; 314; 315; 316; 317; 318; 319; 320; 321; 322; 323; 324; 325; 326; 327; 328; 329; 330; 331; 332; 333; 334; 335; 336; 337; 338; 339; 340; 341; 342; 343; 344; 345; 346; 347; 348; 349; 350 of base pairs. In some embodiments, the nuclear target nucleic acid sequence has 5% of difference with the mitochondrial target nucleic acid sequence. According to the invention a first nucleic acid sequence having at least 5% of difference with a second nucleic acid sequence means that the first sequence has 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of difference with the second amino acid sequence. Nucleic acid sequence difference is typically determined using a suitable sequence alignment algorithm and default parameters, such as BLAST P (Karlin and Altschul, 1990). In some embodiments, the nuclear target nucleic acid sequence has 10% of difference with the mitochondrial target nucleic acid sequence. In some embodiments, the nuclear target nucleic acid sequence has 20% of difference with the mitochondrial target nucleic acid sequence. In some embodiments, the nuclear target nucleic acid sequence has 50% of difference with the mitochondrial target nucleic acid sequence.

As used herein the term "sample" refers to any biological sample obtained from the subject that is liable to contain cell free nucleic acids. Typically, samples include but are not limited to body fluid samples, such as blood, ascite, urine, amniotic fluid, feces, saliva or cerebrospinal fluids. In some embodiments, the sample is a blood sample. By "blood sample" it is meant a volume of whole blood or fraction thereof, e.g., serum, plasma, etc. Any methods well known in the art may be used by the skilled artisan in the art for extracting the free cell nucleic acid from the prepared sample. For example, the method described in the EXAMPLE may be used.

As used herein, the term "primer" refers to an oligonucleotide, whether occurring naturally as in a purified restriction digest or produced synthetically, which is capable of acting as a point of initiation of nucleic acid sequence synthesis when placed under conditions in which synthesis of a primer extension product which is complementary to a nucleic acid strand is induced, i.e. in the presence of different nucleotide triphosphates and a polymerase in an appropriate buffer ("buffer" includes pH, ionic strength, cofactors etc.) and at a suitable temperature. Typically, a primer has a length of 10; 11; 12; 13; 14; 15; 16; 17; 18; 19; 20; 21; 22; 23; 24; 25; 26; 27; 28; 29; or 30 nucleotides. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary to the strand. Primers are typically labelled with a detectable molecule or substance, such as a fluorescent molecule, a radioactive molecule or any others labels known in the art. Labels are known in the art that generally provide (either directly or indirectly) a signal. The term "labelled" is intended to encompass direct labelling of the probe and primers by coupling (i.e., physically linking) a detectable substance as well as indirect labeling by reactivity with another reagent that is directly labeled. Examples of detectable substances include but are not limited to radioactive agents or a fluorophore (e.g. fluorescein isothiocyanate (FITC) or phycoerythrin (PE) or Indocyanine (Cy5)).

Methods (A) Based on the Calculated CmCnDNA Content Ratio

An object of the present invention relates to a method (A) for screening a subject for a cancer comprising the steps of
i) extracting the cell free nucleic acids from a sample obtained from the subject,
ii) determining the total concentration of mitochondrial cell free nucleic acids,
iii) determining the total concentration of nuclear cell free nucleic acids,
iv) calculating the ratio of the level determined at step ii) to the concentration determined at step iii) (CmCnDNA content ratio),
v) comparing ratio determined at step iv) with a predetermined corresponding reference value and
vi) concluding that the subject suffers from a cancer when the ratio determined at step iv) is lower than the predetermined corresponding reference value or concluding that the subject does not suffer from a cancer when the ratio determined at step iv) is higher than the predetermined corresponding reference value.

In some embodiments, the cell free nucleic acids are cell free DNA nucleic acids (ccfDNA). In this embodiment, the ratio of the level determined at step ii) to the level determined at step iii) is typically named as the "CmCnDNA content ratio".

Methods for determining the total concentration of cell free nucleic acids are well known in the art. For example, the method is described in WO2012/028746. Q-PCR is thus the preferred method for determining said concentration.

In some embodiment, the method comprises the steps of a) amplifying and quantifying a nuclear target nucleic acid sequence and b) amplifying and quantifying a mitochondrial target nucleic acid sequence. The CmCnDNA content ratio is thus represented by the ratio of the amplified mitochondrial target nucleic acid sequence to the amplified nuclear target nucleic acid sequence. According to the invention the nuclear target nucleic acid sequence is a sequence which is located in the nucleus human genome. In opposition, the mitochondrial target nucleic acid sequence is a sequence that is present in the mitochondrial human genome (SEQ ID NO:1). Typically the target nucleic acid sequence is part of a coding or non coding sequence. In some embodiments, the mitochondrial target nucleic acid sequence is comprised in the following mitochondrial genes: ND1; ND2; COX1; COX2; ATP8; ATP6; COX3; ND3; ND4L; ND4; ND5; ND6; CYTB; TRNF; TRND; RNR1 TRNV; TRNK; RNR2 TRNL1; TRNS1; TRNI; TRNP; TRNQ; TRNE; TRNM; TRNT TRNW; TRNL2 TRNA; TRNS2; TRNN; TRNR; TRNA; TRNG; TRNN; TRNC; and TRNY. In some embodiments, the target mitochondrial nucleic acid sequence is comprised in a non coding region of the mitochondrial genome such as mitochondrial DNA promoters such as, H1, H2, and L (heavy strand 1, heavy strand 2, and light strand promoters) or mitochondrial control regions or d-loop sequences. The skilled person can thus easily select the appropriate nuclear and mitochondrial target nucleic acid sequences. According to the invention the nuclear and mitochondrial target nucleic acid sequences has about the same length (i.e. size). Typically, the length of the mitochondrial target nucleic acid sequences 1; 2; 3; 4; 5; 6; 7; 8; 9; 10; 11; 12; 13; 14; or 15% longer or shorter than the nuclear target nucleic acid sequence. In some embodiments, both target nucleic acid sequences have the same length. Typically, the target nucleic acid sequences have a length inferior to 110 base pairs. In some embodiments, the target nucleic acid sequence has a length of 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; or 110 base pairs.

In some embodiments, the method (A) of the present invention further comprises the steps of comparing the total concentration of nuclear ccfDNA with a predetermined corresponding reference value ($CnDNA_R$) and concluding that the subject suffers from a cancer when the CmCnDNA content ratio is lower than its predetermined corresponding reference value and the total concentration of nuclear ccfDNA is higher than its predetermined corresponding reference value, or concluding that the subject does not suffer from a cancer when the CmCnDNA content ratio is higher than its predetermined corresponding reference value and the total concentration of nuclear ccfDNA is lower than its predetermined corresponding reference value.

According to the invention, method (A) of the present invention typically involves the use of 2 sets of 2 primers: 1 set of 2 primers (1 sense primer and 1 antisense primer) for amplifying the nuclear target nucleic acid sequence and 1 set of 2 primers (1 sense primer and 1 antisense primer) for amplifying the mitochondrial target nucleic acid sequence.

Methods (B) Based on the DII MITO/DII NUC Ratio

A further object of the present invention relates to a method (B) for screening a subject for a cancer comprising the steps of
i) extracting the cell free nucleic acids from a sample obtained from the subject,
ii) determining the level of the mitochondrial nucleic acids having a length inferior to 110 base pairs,
iii) determining the level of the mitochondrial nucleic acids having a length superior to 250 base pairs,
iv) calculating the ratio of the level determined at step iii) to the level determined at step ii) MITO),
v) determining the level of the nuclear nucleic acids having a length inferior to 110 base pairs,
vi) determining the level of the nuclear nucleic acids having a length superior to 250 base pairs,
vii) calculating the ratio of the level determined at step vi) to the level determined at step v) (DII NUC),
viii) calculation the ratio of the ratio determined at step iv) to the ratio determined at step vii) (DD MITO/DII NUC ratio),
ix) comparing the ratio determined at step viii) with a predetermined corresponding reference value and
x) concluding that the subject suffers from a cancer when the ratio determined at step viii) is higher than the predetermined corresponding reference value or concluding that the subject does not suffer from a cancer when the ratio determined at step viii) is lower than the predetermined corresponding reference value.

In some embodiments, the cell free nucleic acids are cell free DNA nucleic acids (ccfDNA).

Q-PCR is also the preferred method for determining the level of the nucleic acids having a length inferior to 110 base pairs and the level of the nucleic acids having a length of at least 250 base pairs (e.g. see the method is described in WO2012/028746). In some embodiment, the method consists of a) amplifying and quantifying a first mitochondrial target acid nucleic sequence having a length of inferior to 110 base pairs and a second mitochondrial target acid nucleic sequence having a length of at least 250 base pairs and b) amplifying and quantifying a first nuclear target acid nucleic sequence having a length of inferior to 110 base pairs and a second nuclear target acid nucleic sequence having a length of at least 250 base pairs. It is then possible to calculate the ratios between the amplified target acid nucleic sequence having a length of at least 250 base pairs to the amplified target acid nucleic sequence having a length of inferior to 110 base pairs which allows the determination of the ratios determined at steps iv) and vii). In some embodiments, the first (mitochondrial or nuclear) target nucleic acid sequence has a length of 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; or 110 base pairs. In some embodiments, the second (mitochondrial or nuclear) target nucleic acid sequence has a length of 250; 251; 252; 253; 254; 255; 256; 257; 258; 259; 260; 261; 262; 263; 264; 265; 266; 267; 268; 269; 270; 271; 272; 273; 274; 275; 276; 277; 278; 279; 280; 281; 282; 283; 284; 285; 286; 287; 288; 289; 290; 291; 292; 293; 294; 295; 296; 297; 298; 299; 300; 301; 302; 303; 304; 305; 306; 307; 308; 309; 310; 311; 312; 313; 314; 315; 316; 317; 318; 319; 320; 321; 322; 323; 324; 325; 326; 327; 328; 329; 330; 331; 332; 333; 334; 335; 336; 337; 338; 339; 340; 341; 342; 343; 344; 345; 346; 347; 348; 349; 350 base pairs. According to the invention, the first and second (mitochondrial or nuclear) target nucleic acid sequences are located in the same gene. In some embodiments, the first and second (mitochondrial or nuclear) target nucleic sequences are located in the same exon.

According to the invention the ratio of the level of nucleic acids having a length superior to 250 base pairs to the level of the nucleic acids having a length inferior to 110 base pairs is typically named the "DNA Integrity Index" or "DII". It is thus possible to determine the mitochondrial DNA integrity Index ("DII MITO") and the nuclear DNA integrity index ("DII NUC").

In some embodiments, the method (B) of the present invention further comprises the steps of comparing the total concentration of nuclear ccfDNA with a predetermined corresponding reference value ($CnDNA_R$) and concluding that the subject suffers from a cancer when the DII MITO/DII NUC ratio is higher than its predetermined corresponding reference value and the total concentration of nuclear ccfDNA is higher than its predetermined corresponding reference value or concluding that the subject does not suffer from a cancer when the DII MITO/DII NUC ratio is lower than its predetermined corresponding reference value and the total concentration of nuclear ccfDNA is lower than its predetermined corresponding reference value.

According to the invention, method (B) of the present invention typically involves the use of 2 sets of 3 primers: 1 set of 3 primers (1 sense primer and 2 antisense primers) for amplifying the short (<110 bp) and the long (>250 bp) nuclear target nucleic acid sequences and 1 set of 3 primers (1 sense primer and 2 antisense primers) for amplifying the mitochondrial the short (<110 bp) and the long (>250 bp) mitochondrial target nucleic acid sequences.

Combination Methods

In some embodiments, the methods as above described (A) and (B) may be combined. A further object of the present invention relates to a method for screening a subject for a cancer which combines in a single assay performed in a sample obtained from the subject, the determination of the CmCnDNA content ratio, the DII MITO/DII NUC ratio and optionally the total concentration of nuclear ccfDNA. When methods (A) and (B) are combined, the use of 2 sets of 3 primers is sufficient: 1 set of 3 primers (1 sense primer and 2 antisense primers) for amplifying the short (<110 bp) and the long (>250 bp) nuclear target nucleic acid sequences and 1 set of 3 primers (1 sense primer and 2 antisense primers) for amplifying the mitochondrial the short (<110 bp) and the long (>250 bp) mitochondrial target nucleic acid sequences. The comparison between the determined values (e.g. CmCnDNA content ratio, DII MITO/DII NUC ratio . . . ) and the predetermined corresponding values can be performed by computer tools. These computer tools typically involve use of an algorithm for calculating of a score which is the composite of the determined values. The score facilitate the understanding of the results of the comparison steps.

Quantitative PCR (QPCR)

The template nucleic acid need not be purified. Nucleic acids may be extracted from a sample by routine techniques such as those described in Diagnostic Molecular Microbiology: Principles and Applications (Persing et al. (eds), 1993, American Society for Microbiology, Washington D.C.).

U.S. Pat. Nos. 4,683,202, 4,683,195, 4,800,159, and 4,965,188 disclose conventional PCR techniques. PCR typically employs two oligonucleotide primers that bind to a selected target nucleic acid sequence. Primers useful in the present invention include oligonucleotides capable of acting as a point of initiation of nucleic acid synthesis within the target nucleic acid sequence. A primer can be purified from a restriction digest by conventional methods, or it can be produced synthetically. If the template nucleic acid is double-stranded (e.g. DNA), it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min). If the double-stranded template nucleic acid is denatured by heat, the reaction mixture is allowed to cool to a temperature that promotes annealing of each primer to its target sequence on the target nucleic acid sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

QPCR involves use of a thermostable polymerase. The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus,* and *Methanothermus fervidus*. Nonetheless, polymerases that are not thermostable also can be employed in PCR assays provided the enzyme is replenished. Typically, the polymerase is a Taq polymerase (i.e. *Thermus aquaticus* polymerase).

The primers are combined with PCR reagents under reaction conditions that induce primer extension. Typically, chain extension reactions generally include 50 mM KCl, 10 mM Tris-HCl (pH 8.3), 15 mM MgCl2, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target nucleic acid sequence molecule. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Quantitative PCR is typically carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and thermal polymerase.

In order to detect and measure the amount of amplicon (i.e. amplified target nucleic acid sequence) in the sample, a measurable signal has to be generated, which is proportional to the amount of amplified product. All current detection systems use fluorescent technologies. Some of them are non-specific techniques, and consequently only allow the detection of one target at a time. Alternatively, specific detection chemistries can distinguish between non-specific amplification and target amplification. These specific techniques can be used to multiplex the assay, i.e. detecting several different targets in the same assay.

SYBR® Green I:

SYBR® Green I is the most commonly used dye for non-specific detection. It is a double-stranded DNA intercalating dye, that fluoresces once bound to the DNA. A pair of specific primers is required to amplify the target with this chemistry. The amount of dye incorporated is proportional to the amount of generated target. The dye emits at 520 nm and fluorescence emitted can be detected and related to the amount of target. The inconvenience of this technique is that the SYBR® Green I will bind to any amplified dsDNA. Consequently, primer dimers or unspecific products introduce a bias in the quantification. However, it is still possible to check for the specificity of the system by running a meltcurve at the end of the PCR run. The principle is that every product has a different dissociation temperature, depending of the size and base contents, so it is still possible to check the number of products amplified. A valid SYBR® assay—primer pair—should produce a unique, well defined peak on the meltcurve. For these reasons, SYBR® Green I is rarely used for qualitative PCR. However, SYBR® Green I is often used as the first step to optimize a specific detection system assay, to check the specificity of the primers and validate the design.

High Resolution Melting Dyes (HRM Dyes):

High Resolution Meltcurve analysis is a newly emerging technology, which characterizes nucleic acid samples based on their dissociation behaviour. It combines the principle of intercalating dyes, meltcurve analyses and the application of specific statistical analyses. HRM uses the fundamental property of the separation of the two strands of DNA with heat (melting), and the monitoring of this melting with a fluorescent dye. On the contrary of SYBR Green, HRM dyes do not inhibit PCR at high concentration. The dye can consequently saturate the amplified target dsDNA and fluoresces. Melting temperature of a dsDNA target depends on GC content, length, and sequence. Due to the high sensitivity of HRM dyes, even a single base change will induce differences in the melting curve, and consequently in fluorescence (Erali M. et al., 2008). This emerging method is less expensive and as precise than probe-based methods. Only a few thermocyclers on the market currently allow the use of this technology, among them the Roche LightCycler®480, the Corbett Life Science Rotor-Gene™ 6000, and the ABI Prism®7500. The main HRM dyes available are EvaGreen, LCGreen®, SYTO® 9 and BEBO.

TaqMan® Probes=Double-Dye Probes:

TaqMan® probes, also called Double-Dye Oligonucleotides, Double-Dye Probes, or Dual-Labelled probes, are the most widely used type of probes and are often the method of choice for scientists who have just started using Real-Time PCR. They were developed by Roche (Basel, Switzerland) and ABI (Foster City, USA) from an assay that originally used a radio-labelled probe (Holland et al. 1991), which consisted of a single-stranded probe sequence that was complementary to one of the strands of the amplicon. A fluorophore is attached to the 5' end of the probe and a quencher to the 3' end. The fluorophore is excited by the machine and passes its energy, via FRET (Fluorescence Resonance Energy Transfer) to the quencher. Traditionally the FRET pair has been FAM as the fluorophore and TAMRA as the quencher. In a well designed probe, FAM does not fluoresce as it passes its energy onto TAMRA. As TAMRA fluorescence is detected at a different wavelength to FAM, the background level of FAM is low. The probe binds to the amplicon during each annealing step of the PCR. When the Taq polymerase extends from the primer which is bound to the amplicon, it displaces the 5' end of the probe, which is then degraded by the 5'-3' exonuclease activity of the Taq polymerase. Cleavage continues until the remaining probe melts off the amplicon. This process releases the fluorophore and quencher into solution, spatially separating them (compared to when they were held together by the probe). This leads to an irreversible increase in fluorescence from the FAM and a decrease in the TAMRA.

LNA® Double-Dye Probes:

LNA® (Locked Nucleic Acid) was developed by Exiqon® (Vedbaek, Denmark). LNA® changes the conformation of the helix and increases the stability of the duplex. The integration of LNA® bases into Double-Dye Oligonucleotide probes, opens up great opportunities to improve techniques requiring high affinity probes as specific as possible, like SNP detection, expression profiling and in situ hybridization. LNA® is a bicyclic RNA analogue, in which the ribose moiety in the sugar-phosphate backbone is structurally constrained by a methylene bridge between the 2'-oxygen and the 4'-carbon atoms. The integration of LNA® bases into probes changes the conformation of the double helix from the B to A type (Ivanova A. et al., 2007). LNA® conformation allows a much better stacking and therefore a higher stability. By increasing the stability of the duplex, the integration of LNA® monomers into the oligonucleotide sequence allows an increase of the melting Temperature (Tm) of the duplex. It is therefore possible to reduce the size of the probe, which increases the specificity of the probe and helps designing it (Karkare S. et al., 2006).

Molecular Beacon Probes:

Molecular Beacons are probes that contain a stem-loop structure, with a fluorophore and a quencher at their 5' and 3' ends, respectively. The stem is usually 6 bases long, should mainly consist of C's and G's, and holds the probe in the hairpin configuration (Li Y. et al., 2008). The 'stem' sequence keeps the fluorophore and the quencher in close vicinity, but only in the absence of a sequence complementary to the 'loop' sequence. As long as the fluorophore and the quencher are in close proximity, the quencher absorbs any photons emitted by the fluorophore. This phenomenon is called collisional (or proximal) quenching. In the presence of a complementary sequence, the Beacon unfolds and hybridizes to the target, the fluorophore is then displaced from the quencher, so that it can no longer absorb the photons emitted by the fluorophore, and the probe starts to fluoresce. The amount of signal is proportional to the amount of target sequence, and is measured in real time to allow quantification of the amount of target sequence (Takacs T. et al., 2008). The increase in fluorescence that occurs is reversible, (unlike TaqMan® probes), as there is no cleavage of the probe, that can close back into the hairpin structure at low temperature. The stem structure adds specificity to this type of probe, because the hybrid formed between the probe and target has to be stronger than the intramolecular stem association. Good design of Molecular Beacons can give good results, however the signal can be poor, as no physical separation of fluorophore from quencher occurs. Wavelength-Shifting Molecular Beacons are brighter than standard Molecular Beacons due to an enhanced fluorescence intensity of the emitter fluorophore. These probes contain a harvester fluorophore that absorbs strongly in the wavelength range of the monochromatic light source, an emitter fluorophore of the desired emission color, and a non-fluorescent (dark) quencher. In the absence of complementary nucleic acid targets, the probes are non-fluorescent, whereas in the presence of targets, they fluoresce, not in the emission range of the harvester fluorophore, that absorbs the light, but rather in the emission range of the emitter fluorophore. This shift in emission spectrum is due to the transfer of the absorbed energy from the harvester fluorophore to the emitter fluorophore by FRET, which only takes place in probes that are bound to the targets. Wavelength-Shifting Molecular Beacons are substantially brighter than conventional Molecular Beacons that cannot efficiently absorb energy from the available monochromatic light source (Tyagi S. et al., 2000).

Scorpions® Primers:

Scorpions® primers are suitable for both quantitative Real-Time PCR and genotyping/end-point analysis of specific DNA targets. They are PCR primers with a "stem-loop" tail consisting of a specific probe sequence, a fluorophore and a quencher. The "stem-loop" tail is separated from the PCR primer sequence by a "PCR blocker", a chemical modification that prevents the Taq polymerase from copying the stem loop sequence of the Scorpions® primer. Such read-through would lead to non-specific opening of the loop, causing a non-specific fluorescent signal. The hairpin loop is linked to the 5' end of a primer via a PCR blocker. After extension of the primer during PCR amplification, the specific probe sequence is able to bind to its complement within the same strand of DNA. This hybridization event opens the hairpin loop so that fluorescence is no longer quenched and an increase in signal is observed. Unimolecular probing is kinetically favorable and highly efficient. Covalent attachment of the probe to the target amplicon ensures that each probe has a target in the near vicinity. Enzymatic cleavage is not required, thereby reducing the time needed for signaling compared to TaqMan® probes, which must bind and be cleaved before an increase in fluorescence is observed. There are three types of Scorpions® primers. Standard Scorpions®, which consist of a bi-labelled probe with a fluorescent dye at the 5' end and an internal non-fluorescent quencher. FRET Scorpions®, for use on a LightCycler® system. As the capillary system will only excite at 470 nm (FAM absorption wavelength) it is necessary to incorporate a FAM within the stem. A ROX is placed at the 5' end of the Scorpions® primer, FAM is excited and passes its energy onto the ROX. Duplex Scorpions® have also been developed to give much better signal intensity than the normal Scorpions® format. In Standard Scorpions® the quencher and fluorophore remain within the same strand of DNA and some quenching can occur even in the open form. In the Duplex Scorpions® the quencher is on a different oligonucleotide and physical separation between the quencher and fluorophore is greatly increased, reducing the quenching when the probe is bound to the target.

Hybridization Probes (Also Called FRET Probes):

Roche has developed hybridization probes (Caplin et al. 1999) for use with their LightCycler®. Two probes are designed to bind adjacent to one another on the amplicon. One has a 3' label of FAM, whilst the other has a 5' LC dye, LC red 640 or 705. When the probes are not bound to the target sequence, the fluorescent signal from the reporter dye is not detected. However, when the probes hybridize to the target sequence during the PCR annealing step, the close proximity of the two fluorophores allows energy transfer from the donor to the acceptor dye, resulting in a fluorescent signal that is detected.

TaqMan® MGB® Probes:

TaqMan® MGB® probes have been developed by Epoch Biosciences (Bothell, USA) and Applied Biosystems (Foster City, USA). They bind to the minor groove of the DNA helix with strong specificity and affinity. When the TaqMan® MGB® probe is complemented with DNA, it forms a very stable duplex with DNA. The probe carries the MGB® moiety at the 3' end. The MGB strongly increases the probe Tm, allowing shorter, hence more specific designs. The probe performs particularly well with A/T rich regions, and is very successful for SNP detection (Walburger et al., 2001). It can also be a good alternative when trying to design a probe which should be located in the splice junction (for which conventional probes are hard to design). Smaller probes can be designed with Tm as 65-67° C., which gives a better discrimination (the probe is more specific for single mismatch). A good alternative to MGB probes are LNA® probes where the increase in Tm induced by the addition of LNA® bases is specific, contrary to the MGB moiety (cf p. 15). During the primer extension step, the hybridized probe is cleaved by the 5' exonuclease activity of Taq polymerase and an increase in fluorescence is seen. Fluorescence of the cleaved probe during PCR is monitored in Real-Time by the thermocycler.

MGB Eclipse® Probes:

MGB Eclipse® probes also known as QuantiProbes, have originally been developed by Epoch Biosciences (Bothell, USA). MGB Eclipse® probes carry a minor groove binder moiety that allows the use of short probes for very high specificity. These are short linear probes that have a minor groove binder and a quencher on the 5' end and a fluorophore on the 3'end. This is the opposite orientation to TaqMan® MGB® probes and it is thought that the minor groove binder prevents the exonuclease activity of the Taq polymerase from cleaving the probe. The quencher is a Non Fluorescent Quencher also known as Eclipse Dark Quencher. Quenching occurs when the random coiling of the probe in the free form brings the quencher and the fluorophore close to another. The probe is straightened out when bound to its target and quenching is decreased, leading to an increase in fluorescent signal. The technologies that have been discussed above are the most widely used today, but numerous other technologies have occurred in publications, or are available on the market, such as: Resonsense probes, Light-up probes, HyBeacon® probes, LUX primers, Yin-yang probes, or Amplifluor®. You can contact us for more information on any of them.

The majority of the thermocyclers on the market now offer similar characteristics. Typically, thermocyclers involve a format of glass capillaries, plastics tubes, 96-well plates or 384-wells plates. The thermocylcer also involve a software analysis.

Typically quantitative PCR involves use of:

Taq polymerase: A HotStart Taq polymerase is inactive at low temperatures (room temperature). Heating at 95° C. for several—usually 5 to 10—minutes activates the enzyme, and the amplification can begin once the primers are annealed. The enzyme is not active until the entire DNA is denatured. Two major HotStart modifications exist, the antibody-blocked Taq and the chemically-blocked Taq. The antibody-blocked Taq is inactive because it is bound to a thermolabile inhibitor that is denatured during the initial step of PCR. The chemically-blocked Taq provides one clear advantage over the antibody-blocked Taq, as it is completely inactive at 60° C., (the hybridization temperature of primers), thus preventing the formation of non-specific amplification and reducing primer dimer formation.

dNTps/dUTps: Some kits contain a blend of dNTPs and dUTPs, other ones contain only dNTPs. Using only dNTPs increases the sensitivity, the reason being that the Taq incorporates more easily dNTPs than dUTPs. However, using a mix containing dUTPs brings security to the assay, in case of contamination from a previous PCR product. Thanks to the UNG activity in association with incorporated dUTPs, this contamination can be eliminated.

Uracil-N-Glycosylase: The Uracil-N-Glycosylase is an enzyme that hydrolyses all single-stranded and double-stranded DNA containing dUTPs. Consequently, if all PCR amplifications are performed in the presence of a dNTPs/dUTPs blend, by carrying a UNG step before every run it is possible to get rid of any previous PCR product.

ROX reference dye: Some thermocyclers require Master-Mix containing ROX dye for normalization. This is the case for the ABI and Eppendorf machines, and optional on the Stratagene machines. If you work with such machines, it is easier to work with the ROX dye already incorporated in the MasterMix rather than adding it manually. It guarantees a higher level of reproducibility and homogeneity of your assays.

Fluorescein: For iCycler iQ®, My iQ® and iQ5 machines (BioRad thermocyclers), the normalization method for SYBR® Green assay uses Fluorescein to create a "virtual background". As in the case for the ROX, it is better and easier to use a MasterMix that contains pre-diluted Fluorescein, guaranteeing higher reproducibility and homogeneity of your assays.

MgCl$_2$: MgCl$_2$ is necessary for the Taq activity. MgCl concentration in MasterMixes is optimized according to the amount of Taq and also the buffer composition. However, it may be necessary sometimes to add MgCl2 and most MasterMixes include an additional tube of MgCl2.

Inert colored dye: Some buffers also include an inert colored dye, to enable visualization of the buffer when loading in the wells. This colored dye has no effect on the sensitivity of the assay and is a convenient working tool. Note that such mixes, in combination with white plastic plates, provide better levels of fluorescence and a really easy way of working.

Well-designed primers and probes are a prerequisite for successful quantitative PCR. By using well-designed primers and probes, PCR efficiencies of 100% can be obtained. Typically primers are designed using a design software (for example Oligo® Primer Analysis Software). Most thermocycler softwares now offer tools to help in designing primers with the best characteristics. Some of the best softwares are Beacon Designer, Primer Express, and DNA Star . . . . Some other tools are freely available on the web, for example:

http://medgen.ugent.be/rtprimerdb/(human primer and probe database)
http://frontend.bioinfo.rpi.edu/applications/mfold/ (for testing secondary structures)
http://www.ebi.ac.uk/~lenov/meltinghome.html (Tm calculators)
http://frodo.wi.mit.edu/cgi-bin/primer/primer3_www.cgi
http://bibiserv.techfak.uni-bielefeld.de/genefisher2
http://www.premierbiosoft.com/qper/index Typically, Q PCR involves the preparation of a standard curve for each amplified target nucleic acid sequence. Preparing a standard curve can indeed provide a good idea of the performance of the qPCR and thus serves as a quality control. The standard curve should cover the complete range of expected expression. Using standard material the standard curve should include at least 5 points of dilution, each of them in duplicate (at least). The 10-fold or 2-fold dilution range should cover the largest range of expression levels. Plotting these points on a standard curve, will determine the linearity, the efficiency, the sensitivity and the reproducibility of the assay. According to the present invention the standard curve is prepared from a genomic DNA sample. As used herein, "genomic DNA sample" or "gDNA" refers to a genomic DNA sample prepared from a DNA preparation. Methods for DNA purification are well known in the art. The genomic DNA may be prepared from a cell that is of the same organism than the cell that is used for preparing the nucleic acid sample of the invention (i.e. a human cell). Furthermore the cell from which the genomic sample is prepared must present the same ploidy than the cell used for preparing the nucleic acid sample of the invention; i.e. the cells present the same chromosomal abnormalities (e.g. in case of cancer cells). Typically, the genomic DNA sample is prepared from a cell for which the DII as defined above is about 1.

Predetermined Corresponding Reference Values

Typically, the predetermined corresponding reference value can be relative to a number or value derived from population studies, including without limitation, subjects of the same or similar age range, subjects in the same or similar ethnic group, subjects at risk of cancer, and subjects having the same severity of cancer. Such predetermined corresponding reference values can be derived from statistical analyses and/or risk prediction data of populations obtained from mathematical algorithms and computed indices of the disease.

Typically, the predetermined corresponding reference value is a threshold value or a cut-off value. A "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of the expression level of the marker of interest (e.g. CmCnDNA content ratio, DII MITO/DII NUC ratio, total concentration of nuclear ccfDNA) in properly banked historical subject samples may be used in establishing the predetermined corresponding reference value. In some embodiments, the predetermined corresponding reference value is the median measured in the population of the subjects for the marker of interest (e.g. CmCnDNA content ratio, DII MITO/DII NUC ratio, total concentration of nuclear ccfDNA). In some embodiments, the threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the expression level of the marker of interest (e.g. CmCnDNA content ratio, DII MITO/DII NUC ratio, total concentration of nuclear ccfDNA) in a group of reference, one can use algorithmic analysis for the statistic treatment of the expression levels determined in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator the reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

In some embodiments, the predetermined corresponding reference value is typically determined by carrying out a method comprising the steps of:

a) providing a collection of samples from subjects;

b) providing, for each sample provided at step a), information relating to the actual clinical profile of the subject (healthy or suffering from a cancer);

c) providing a serial of arbitrary quantification values;

d) determining the level of the marker of interest (e.g. CmCnDNA content ratio, DII MITO/DII NUC ratio, total concentration of nuclear ccfDNA) for each sample contained in the collection provided at step a);

e) classifying said blood samples in two groups for one specific arbitrary quantification value provided at step c), respectively: (i) a first group comprising samples that exhibit a quantification value for level that is lower than the said arbitrary quantification value contained in the said serial of quantification values; (ii) a second group comprising samples that exhibit a quantification value for said level that is higher than the said arbitrary quantification value contained in the said serial of quantification values; whereby two groups of samples are obtained for the said specific quantification value, wherein the samples of each group are separately enumerated;

f) calculating the statistical significance between (i) the quantification value obtained at step e) and (ii) the actual clinical profile of the subjects from which samples contained in the first and second groups defined at step f) derive;

g) reiterating steps f) and g) until every arbitrary quantification value provided at step d) is tested;

h) setting the said predetermined corresponding reference value as consisting of the arbitrary quantification value for which the highest statistical significance (most significant) has been calculated at step g).

Thus in some embodiments, the predetermined corresponding reference value thus allows discrimination between healthy subject and subjects suffering from cancer. Practically, high statistical significance values (e.g. low P values) are generally obtained for a range of successive arbitrary quantification values, and not only for a single arbitrary quantification value. Thus, in one alternative embodiment of the invention, instead of using a definite predetermined corresponding reference value, a range of values is provided. Therefore, a minimal statistical significance value (minimal threshold of significance, e.g. maximal threshold P value) is arbitrarily set and a range of a plurality of arbitrary quantification values for which the statistical significance value calculated at step g) is higher (more significant, e.g. lower P value) are retained, so that a range of quantification values is provided. This range of quantification values includes a "cut-off" value as described above. For example, according to this specific embodiment of a "cut-off" value, the diagnosis can be determined by comparing the level of the marker of interest (e.g. CmCnDNA content ratio, DII MITO/DII NUC ratio, total concentration of nuclear ccfDNA) with the range of values which are identified. In certain embodiments, a cut-off value thus consists of a range of quantification values, e.g. centered on the quantification value for which the highest statistical significance value is found (e.g. generally the minimum p value which is found). For example, on a hypothetical scale of 1 to 10, if the ideal cut-off value (the value with the highest statistical significance) is 5, a suitable (exemplary) range may be from 4-6. Therefore, a subject may be assessed by comparing values obtained by measuring the level of the marker of interest (e.g. CmCnDNA content ratio, DII MITO/DII NUC ratio, total concentration of nuclear ccfDNA), where values higher (or lower depending on the selected marker) than 5 reveal that the subject suffers from cancer and values lower (or higher depending on the selected marker) than 5 reveal that the subject does not suffer from a cancer. In some embodiments, a subject may be screened for a cancer by comparing values obtained by measuring the level of the marker of interest (e.g. CmCnDNA content ratio, DII MITO/DII NUC ratio, total concentration of nuclear ccfDNA) and comparing the values on a scale, where values above (or below depending on the selected marker) the range of 4-6 indicate that the subject suffers from a cancer and values below or above depending on the selected marker) the range of 4-6 indicate that the subject does not suffer from a cancer, with values falling within the range of 4-6 indicate that further investigation are needed for determining whether the subject suffers from a cancer.

Therapeutic Applications

The method of the present invention allows discriminating healthy subjects from subjects suffering from a cancer. Then, the origin of the cancer is sought in the subject for determining its location and stage. Method for investigation the location of the cancer typically involves imaging techniques. Once the cancer is located in the subject, further investigations such as biopsies could be performed for determining the origin, the dissemination and the stage of the cancer.

The methods of the present invention can also be suitable for determining whether a subject is eligible or not to an anti-cancer treatment. An anti-cancer treatment typically consists of radiotherapy, chemotherapy, immunotherapy or a combination thereof. The treatment can also consist of an adjuvant therapy (i.e. treatment after chirurgical resection of the primary tumor) of a neoadjuvant therapy (i.e. treatment before chirurgical resection of the primary tumor).

In some embodiments, the methods of the present invention are suitable for determining whether a subject is eligible or not to a treatment with a chemotherapeutic agent. For example, when it is concluded that the subject has a poor diagnosis then the physician can take the choice to administer the subject with a chemotherapeutic agent.

The term "chemotherapeutic agent" refers to chemical compounds that are effective in inhibiting tumor growth. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoraramide and trimethylolomelamine; acetogenins (especially bullatacin and bullatacinone); a carnptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estrarnustine, ifosfamide, mechlorethamine, mechlorethamine oxide hydrochloride, melphalan, novembichin, phenesterine, prednimus tine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin (11 and calicheamicin 211, see, e.g., Agnew Chem Intl. Ed. Engl. 33:183-186 (1994); dynemicin, including dynemicin A; an esperamicin; as well as neocarzinostatin chromophore and related chromoprotein enediyne antiobiotic chromomophores), aclacinomysins, actinomycin, authramycin, azaserine, bleomycins, cactinomycin, carabicin, canninomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idanrbicin, marcellomycin, mitomycins, mycophenolic acid, nogalarnycin, olivomycins, peplomycin, potfiromycin, puromycin, quelamycin, rodorubicin, streptomgrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophospharnide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pento statin; phenamet; pirarubicin; podophyllinic acid; 2-ethylhydrazide; procarbazine; PSK®; razoxane; rhizoxin; sizofiran; spirogennanium; tenuazonic acid; triaziquone; 2,2',2"-trichlorotriethylarnine; trichothecenes (especially T-2 toxin, verracurin A, roridinA and anguidine); urethan; vindesine; dacarbazine; mannomustine; mitobromtol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.].) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are antihormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

In some embodiments, the methods of the present invention are suitable for determining whether a subject is eligible or not to targeted therapy. For example, when it is concluded that the subject has a poor diagnosis then the physician can take the choice to administer the subject with a targeted therapy.

Targeted cancer therapies are drugs or other substances that block the growth and spread of cancer by interfering with specific molecules ("molecular targets") that are involved in the growth, progression, and spread of cancer. Targeted cancer therapies are sometimes called "molecularly targeted drugs," "molecularly targeted therapies," "precision medicines," or similar names.

In some embodiments, the targeted therapy consists of administering the subject with a tyrosine kinase inhibitor. The term "tyrosine kinase inhibitor" refers to any of a variety of therapeutic agents or drugs that act as selective or non-selective inhibitors of receptor and/or non-receptor tyrosine kinases. Tyrosine kinase inhibitors and related compounds are well known in the art and described in U.S. Patent Publication 2007/0254295, which is incorporated by reference herein in its entirety. It will be appreciated by one of skill in the art that a compound related to a tyrosine kinase inhibitor will recapitulate the effect of the tyrosine kinase inhibitor, e.g., the related compound will act on a different member of the tyrosine kinase signaling pathway to produce the same effect as would a tyrosine kinase inhibitor of that tyrosine kinase. Examples of tyrosine kinase inhibitors and related compounds suitable for use in methods of embodiments of the present invention include, but are not limited to, dasatinib (BMS-354825), PP2, BEZ235, saracatinib, gefitinib (Iressa), sunitinib (Sutent; SU11248), erlotinib (Tarceva; OSI-1774), lapatinib (GW572016; GW2016), canertinib (CI 1033), semaxinib (SU5416), vatalanib (PTK787/ZK222584), sorafenib (BAY 43-9006), imatinib (Gleevec; STI571), leflunomide (SU101), vandetanib (Zactima; ZD6474), MK-2206 (8-[4-aminocyclobutyl)phenyl]-9-phenyl-1,2,4-triazolo[3,4-f][1,6]naphthyridin-3(2H)-one hydrochloride) derivatives thereof, analogs thereof, and combinations thereof. Additional tyrosine kinase inhibitors and related compounds suitable for use in the present invention are described in, for example, U.S. Patent Publication 2007/0254295, U.S. Pat. Nos. 5,618,829, 5,639,757, 5,728,868, 5,804,396, 6,100,254, 6,127,374, 6,245,759, 6,306,874, 6,313,138, 6,316,444, 6,329,380, 6,344,459, 6,420,382, 6,479,512, 6,498,165, 6,544,988, 6,562,818, 6,586,423, 6,586,424, 6,740,665, 6,794,393, 6,875,767, 6,927,293, and 6,958,340, all of which are incorporated by reference herein in their entirety. In certain embodiments, the tyrosine kinase inhibitor is a small molecule kinase inhibitor that has been orally administered and that has been the subject of at least one Phase I clinical trial, more preferably at least one Phase II clinical, even more preferably at least one Phase III clinical trial, and most preferably approved by the FDA for at least one hematological or oncological indication. Examples of such inhibitors include, but are not limited to, Gefitinib, Erlotinib, Lapatinib, Canertinib, BMS-599626 (AC-480), Neratinib, KRN-633, CEP-11981, Imatinib, Nilotinib, Dasatinib, AZM-475271, CP-724714, TAK-165, Sunitinib, Vatalanib, CP-547632, Vandetanib, Bosutinib, Lestaurtinib, Tandutinib, Midostaurin, Enzastaurin, AEE-788, Pazopanib, Axitinib, Motasenib, OSI-930, Cediranib, KRN-951, Dovitinib, Seliciclib, SNS-032, PD-0332991, MKC-I (Ro-317453; R-440), Sorafenib, ABT-869, Brivanib (BMS-582664), SU-14813, Telatinib, SU-6668, (TSU-68), L-21649, MLN-8054, AEW-541, and PD-0325901.

In some embodiments, the methods of the present invention are suitable for determining whether a subject is eligible or not to a treatment with an immunotherapeutic agent. For example, when it is concluded that the subject has a poor diagnosis then the physician can take the choice to administer the subject with an immunotherapeutic agent.

The term "immunotherapeutic agent," as used herein, refers to a compound, composition or treatment that indirectly or directly enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T cells, NK, cells, dendritic cells, B cells . . . ).

Immunotherapeutic agents can be non-specific, i.e. boost the immune system generally so that the human body becomes more effective in fighting the growth and/or spread of cancer cells, or they can be specific, i.e. targeted to the cancer cells themselves immunotherapy regimens may combine the use of non-specific and specific immunotherapeutic agents.

Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g. cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants.

A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors.

Interferons (IFNs) contemplated by the present invention include the common types of IFNs, IFN-alpha (IFN-a), IFN-beta (IFN-beta) and IFN-gamma (IFN-y). IFNs can act directly on cancer cells, for example, by slowing their growth, promoting their development into cells with more normal behaviour and/or increasing their production of antigens thus making the cancer cells easier for the immune system to recognise and destroy. IFNs can also act indirectly on cancer cells, for example, by slowing down angiogenesis, boosting the immune system and/or stimulating natural killer (NK) cells, T cells and macrophages. Recombinant IFN-alpha is available commercially as Roferon (Roche Pharmaceuticals) and Intron A (Schering Corporation). The use of IFN-alpha, alone or in combination with other immunotherapeutics or with chemotherapeutics, has shown efficacy in the treatment of various cancers including melanoma (including metastatic melanoma), renal cancer (including metastatic renal cancer), breast cancer, prostate cancer, and cervical cancer (including metastatic cervical cancer).

Interleukins contemplated by the present invention include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present invention. Interleukins, alone or in combination with other immunotherapeutics or with chemotherapeutics, have shown efficacy in the treatment of various cancers including renal cancer (including metastatic renal cancer), melanoma (including metastatic melanoma), ovarian cancer (including recurrent ovarian cancer), cervical cancer (including metastatic cervical cancer), breast cancer, colorectal cancer, lung cancer, brain cancer, and prostate cancer.

Interleukins have also shown good activity in combination with IFN-alpha in the treatment of various cancers (Negrier et al., Ann Oncol. 2002 13(9):1460-8; Tourani et al, J. Clin. Oncol. 2003 21(21):398794).

Colony-stimulating factors (CSFs) contemplated by the present invention include granulocyte colony stimulating factor (G-CSF or filgrastim), granulocyte-macrophage colony stimulating factor (GM-CSF or sargramostim) and erythropoietin (epoetin alfa, darbepoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Arnesp (erytropoietin). Colony stimulating factors have shown efficacy in the treatment of cancer, including melanoma, colorectal cancer (including metastatic colorectal cancer), and lung cancer.

Non-cytokine adjuvants suitable for use in the combinations of the present invention include, but are not limited to, Levamisole, alum hydroxide (alum), Calmette-Guerin *bacillus* (ACG), incomplete Freund's Adjuvant (IFA), QS-21, DETOX, Keyhole limpet hemocyanin (KLH) and dinitrophenyl (DNP). Non-cytokine adjuvants in combination with other immuno- and/or chemotherapeutics have demonstrated efficacy against various cancers including, for example, colon cancer and colorectal cancer (Levimasole); melanoma (BCG and QS-21); renal cancer and bladder cancer (BCG).

In addition to having specific or non-specific targets, immunotherapeutic agents can be active, i.e. stimulate the body's own immune response, or they can be passive, i.e. comprise immune system components that were generated external to the body.

Passive specific immunotherapy typically involves the use of one or more monoclonal antibodies that are specific for a particular antigen found on the surface of a cancer cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins.

Monoclonal antibodies currently used as cancer immunotherapeutic agents that are suitable for inclusion in the combinations of the present invention include, but are not limited to, rituximab (Rituxan®), trastuzumab (Herceptin®), ibritumomab tiuxetan (Zevalin®), tositumomab (Bexxar®), cetuximab (C-225, Erbitux®), bevacizumab (Avastin®), gemtuzumab ozogamicin (Mylotarg®), alemtuzumab (Campath®), and BL22. Monoclonal antibodies are used in the treatment of a wide range of cancers including breast cancer (including advanced metastatic breast cancer), colorectal cancer (including advanced and/or metastatic colorectal cancer), ovarian cancer, lung cancer, prostate cancer, cervical cancer, melanoma and brain tumours. Other examples include anti-CTLA4 antibodies (e.g. Ipilimumab), anti-PD1 antibodies, anti-PDL1 antibodies, anti-TIMP3 antibodies, anti-LAG3 antibodies, anti-B7H3 antibodies, anti-B7H4 antibodies or anti-B7H6 antibodies.

Active specific immunotherapy typically involves the use of cancer vaccines. Cancer vaccines have been developed that comprise whole cancer cells, parts of cancer cells or one or more antigens derived from cancer cells. Cancer vaccines, alone or in combination with one or more immuno- or chemotherapeutic agents are being investigated in the treatment of several types of cancer including melanoma, renal cancer, ovarian cancer, breast cancer, colorectal cancer, and lung cancer. Non-specific immunotherapeutics are useful in combination with cancer vaccines in order to enhance the body's immune response.

The immunotherapeutic treatment may consist of an adoptive immunotherapy as described by Nicholas P. Restifo, Mark E. Dudley and Steven A. Rosenberg "Adoptive immunotherapy for cancer: harnessing the T cell response, Nature Reviews Immunology, Volume 12, April 2012). In adoptive immunotherapy, the subject's circulating lymphocytes, or tumor infiltrated lymphocytes, are isolated in vitro, activated by lymphokines such as IL-2 or transuded with genes for tumor necrosis, and readministered (Rosenberg et al., 1988; 1989). The activated lymphocytes are most preferably be the subject's own cells that were earlier isolated from a blood or tumor sample and activated (or "expanded") in vitro. This form of immunotherapy has produced several cases of regression of melanoma and renal carcinoma.

In some embodiments, the methods of the present invention are suitable for determining whether a subject is eligible or not to a treatment with a radiotherapeutic agent. For example, when it is concluded that the subject has a poor diagnosis then the physician can take the choice to administer the subject with a radiotherapeutic agent.

The term "radiotherapeutic agent" as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, and/or another radiotherapy.

The methods of the present invention are also suitable for determining the efficiency of an above mentioned treatment in the subject.

In particular, the present invention further relates to a method for determining whether a subject achieve a response with a treatment (as above mentioned) comprising the steps (or one of each) of i) determining the CmCnDNA content ratio before the treatment ii) determining the CmCnDNA content ratio after the treatment iii) comparing the CmCnDNA content ratio determined at step i) with the CmCnDNA content ratio determined at step ii) and concluding that the subject achieves a response with his treatment when the CmCnDNA content ratio determined at step ii) is higher than the CmCnDNA content ratio determined at step i) or concluding that the subject does not achieve a response with his treatment when the CmCnDNA content ratio determined at step ii) is above the same or lower than the CmCnDNA content ratio determined at step i).

In particular, the present invention further relates to a method for determining whether a subject achieve a response with a treatment (as above mentioned) comprising the steps of i) determining the DII MITO/DII NUC ratio before the treatment ii) determining the DII MITO/DII NUC ratio after the treatment iii) comparing the DII MITO/DII NUC ratio determined at step i) with the DII MITO/DII NUC ratio determined at step ii) and concluding that the subject achieves a response with his treatment when the DII MITO/DII NUC ratio determined at step ii) is lower than the DII MITO/DII NUC ratio determined at step i) or concluding that the subject does not achieve a response with his treatment when the DII MITO/DII NUC ratio determined at step ii) is above the same or higher than the DII MITO/DII NUC ratio determined at step i).

In particular, the present invention further relates to a method for determining whether a subject achieve a response with a treatment (as above mentioned) comprising the steps (or one of each) of i) determining the CmCnDNA content ratio before the treatment ii) determining the CmCnDNA content ratio after the treatment iii) comparing the CmCnDNA content ratio determined at step i) with the CmCnDNA content ratio determined at step ii) and concluding that the subject achieves a response with his treatment when the CmCnDNA content ratio determined at step ii) is higher than the CmCnDNA content ratio determined at step i) or concluding that the subject does not achieve a response with his treatment when the CmCnDNA content ratio determined at step ii) is above the same or lower than the CmCnDNA content ratio determined at step i).

In particular, the present invention further relates to a method for determining whether a subject achieve a response with a treatment (as above mentioned) comprising the steps of i) determining the DII MITO/DII NUC ratio before the treatment ii) determining the DII MITO/DII NUC ratio after the treatment iii) comparing the DII MITO/DII NUC ratio determined at step i) with the DII MITO/DII NUC ratio determined at step ii) and concluding that the subject achieves a response with his treatment when the DII MITO/DII NUC ratio determined at step ii) is lower than the DII MITO/DII NUC ratio determined at step i) or concluding that the subject does not achieve a response with his treatment when the DII MITO/DII NUC ratio determined at step ii) is above the same or higher than the DII MITO/DII NUC ratio determined at step i).

The above mentioned methods of the present invention are particularly suitable for discriminating responder from non responder. As used herein the term "responder" in the context of the present disclosure refers to a subject that will achieve a response, i.e. a subject where the cancer is eradicated, reduced or improved, or stabilized such that the disease is not progressing after the treatment. In responders where the cancer is stabilized, the period of stabilization is such that the quality of life and/or subjects' life expectancy is increased (for example stable disease for more than 6, 7, 8, 9, 10, 11, 12, 13, 14, 15, 16, 17, 18, 19, 20, 21, 22, 23, 24 or more months) in comparison to a subject that does not receive the treatment. A non-responder or refractory subject includes subjects for whom the cancer does not show reduction or improvement after treatment. Optionally the characterization of the subject as a responder or non-responder can be performed by reference to a standard or a training set. The standard may be the profile of a subject who is known to be a responder or non responder or alternatively may be a numerical value. Such predetermined standards may be provided in any suitable form, such as a printed list or diagram, computer software program, or other media. When it is concluded that the subject is a non responder, the physician could take the decision to stop the treatment to avoid any further adverse sides effects.

In particular, the present invention further relates to a method for determining whether a subject who suffered from a cancer has a relapse after a treatment (as above mentioned and including resection of the tumor) comprising the steps (or one of each) of i) determining the CmCnDNA content ratio after the treatment ii) comparing the CmCnDNA content ratio determined at step i) with a predetermined corresponding reference value iii) and concluding that the subject has a relapse when the CmCnDNA content ratio determined at step i) is lower than the predetermined corresponding reference value or concluding that the subject has not relapsed when the CmCnDNA content ratio determined at step i) is higher than the predetermined corresponding reference value.

In particular, the present invention further relates to a method for determining whether a subject who suffered from a cancer has a relapse after a treatment (as above mentioned and including resection of the tumor) comprising the steps of i) determining the DII MITO/DII NUC ratio ii) comparing the DII MITO/DII NUC ratio determined at step i) with a predetermined corresponding reference value and iii) concluding that the subject has a relapse when the DII MITO/DII NUC ratio determined at step i) is higher than the predetermined corresponding reference value or concluding that the subject has not relapsed when the DII MITO/DII NUC ratio determined at step i) is lower than the predetermined corresponding reference value.

As used herein, the term "relapse" refers to the return of a cancer or the signs and symptoms of a cancer after a period of improvement in which no cancer could be detected. The likely relapse occurs is that a few of the original cancer cells survived the initial treatment. Sometimes, this is because cancer cells spread to other parts of the body and were too small to be detected during the follow-up taking place after the treatment (metastasis).

Typically, the CmCnDNA content ratio and/or the DII MITO/DII NUC ratio is determined after 6, 7, 8, 9, 10, 11, 12, 13, 14, 15, 16, 17, 18, 19, 20, 21, 22, 23, 24 months or more after the end of the treatment.

The invention will be further illustrated by the following figures and examples. However, these examples and figures should not be interpreted in any way as limiting the scope of the present invention.

FIGURES

Figure 1:
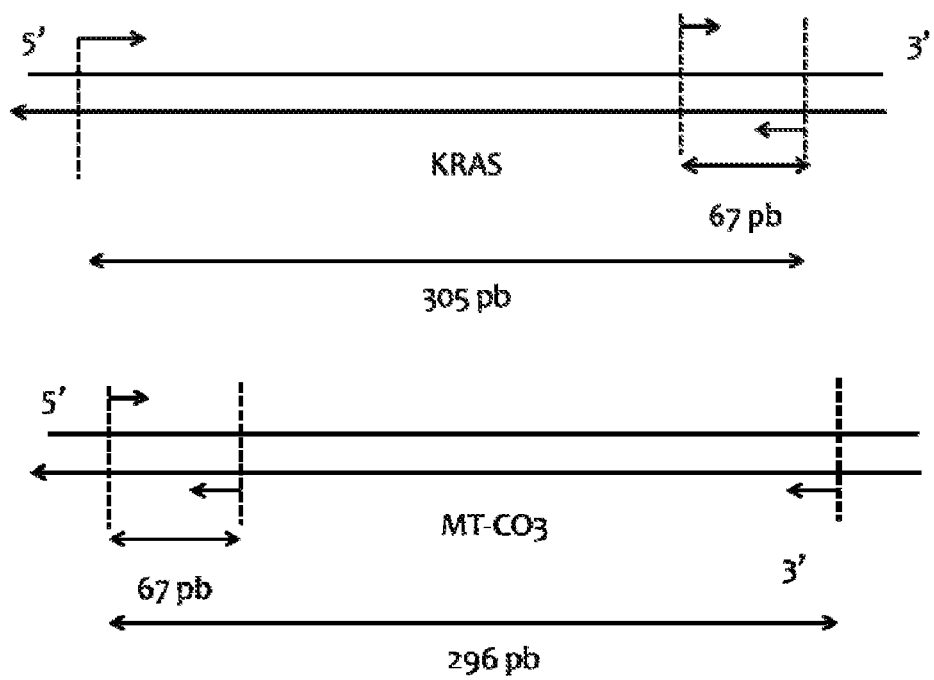

FIG. 1: Primer set design to study quantification and fragmentation of nuclear and mitochondrial DNA.

FIG. 2: A. Dot plot of the CmCnDNA content ratio in blood of healthy individuals (n=80) and in CRC patients from stage I to IV (n=146). B. Dot plot of the CmCnDNA content ratio in blood of healthy individuals (n=80) and in stage I/II/III CRC patients (n=74). C. Dot plot of the CmCnDNA content ratio in blood of healthy individuals (n=80) and in stage I/II/III CRC patients (n=72).

FIG. 3: A. Diagnosis predictive capacity of CmCnDNA content ratio to distinguish plasma from CRC patients (n=138) and healthy subjects (n=80). ROC Curve representation deriving from the univariate logistic analysis corresponding to total ccfDNA (AUC=0.98). B. Diagnosis predictive capacity of CmCnDNA content ratio to distinguish plasmas from stage I-III CRC patients (n=74) and healthy subjects (n=80). ROC Curve representation deriving from the univariate logistic analysis corresponding to total ccfDNA (AUC=0.98). C. Diagnosis predictive capacity of CmCnDNA content ratio to distinguish plasmas from stage IV CRC patients (n=72) and healthy subjects (n=80). ROC Curve representation deriving from the univariate logistic analysis corresponding to total ccfDNA (AUC=0.98).

Figure 4:
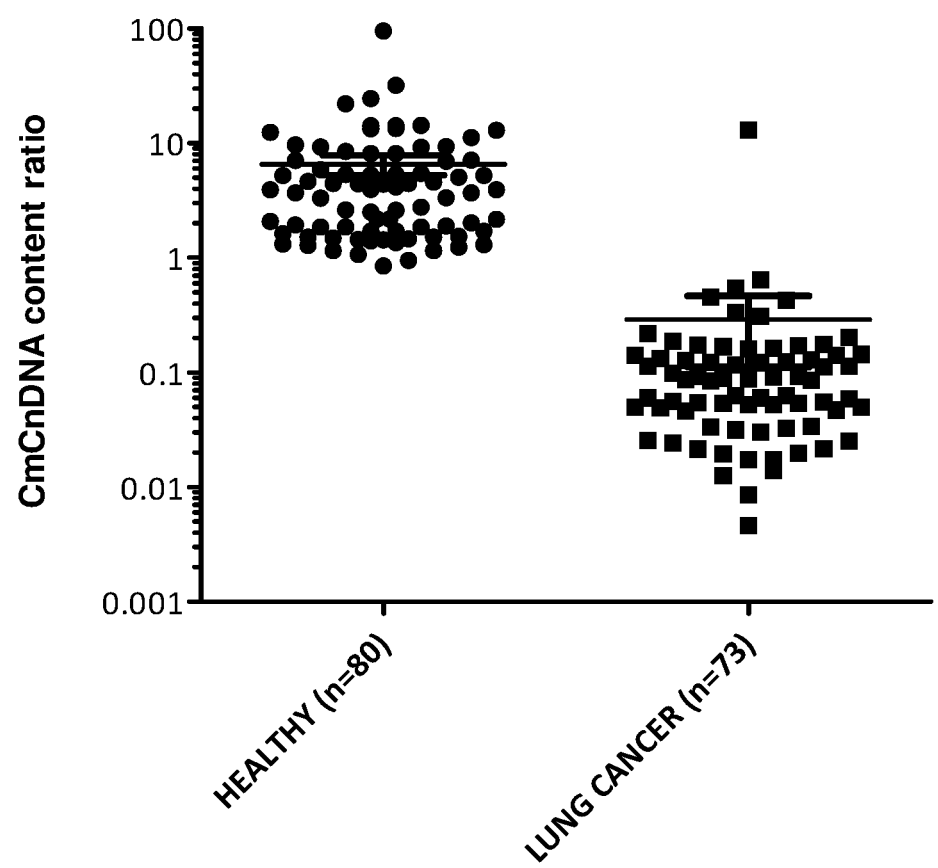

FIG. 4: Dot plot of the CmCnDNA content ratio in blood of healthy individuals (n=80) and in lung cancer patients from stage I to IV (n=73).

Figure 5:
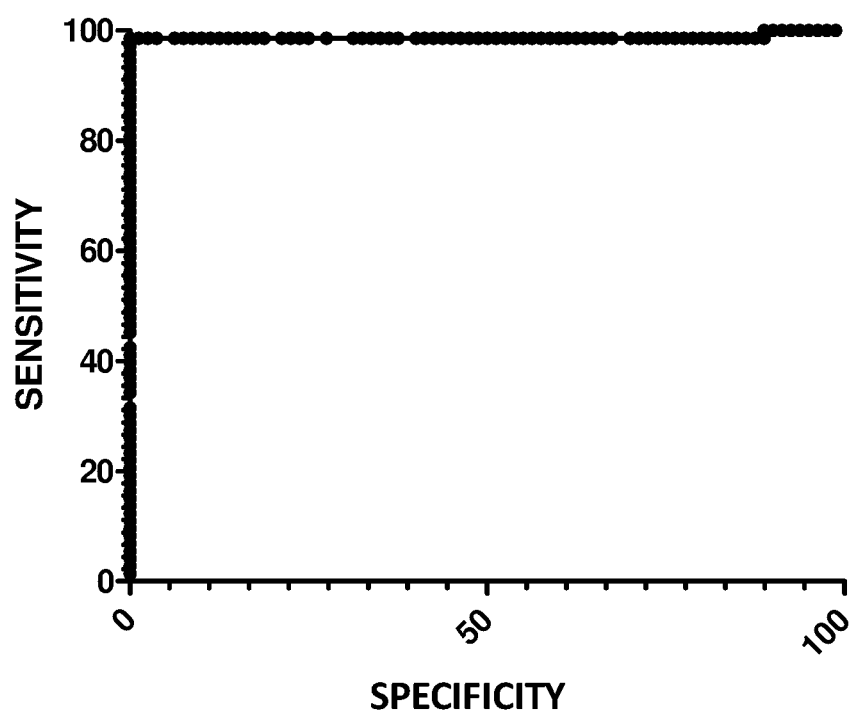

FIG. 5: Diagnosis predictive capacity of CmCnDNA content ratio to distinguish plasma from lung cancer patients (n=73) and healthy subjects (n=80). ROC Curve representation deriving from the univariate logistic analysis corresponding to total ccfDNA (AUC=0.99).

Figure 6:
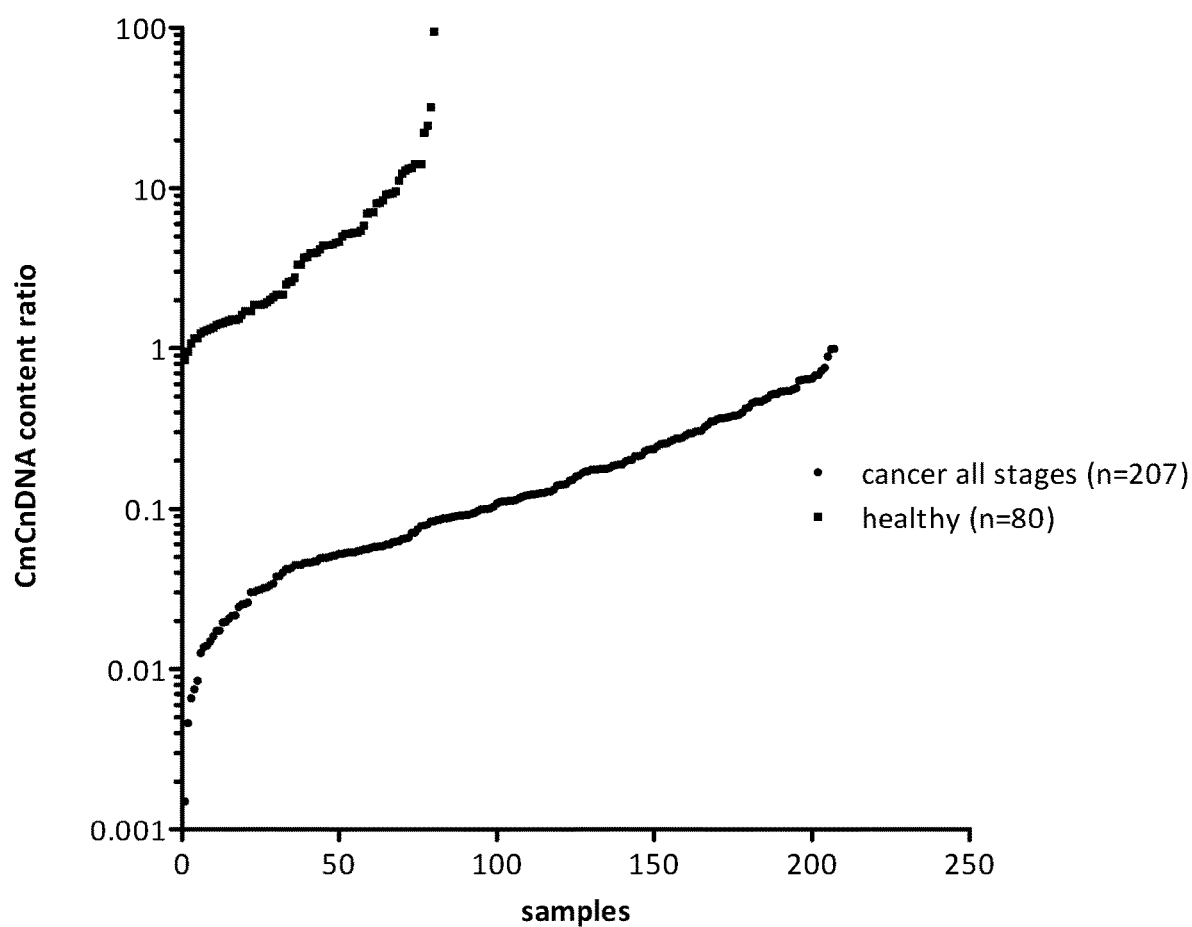

FIG. 6: Values of CmCnDNA content ratio determined in plasma of cancer patients (circle) and healthy individuals (square).

Figure 7:
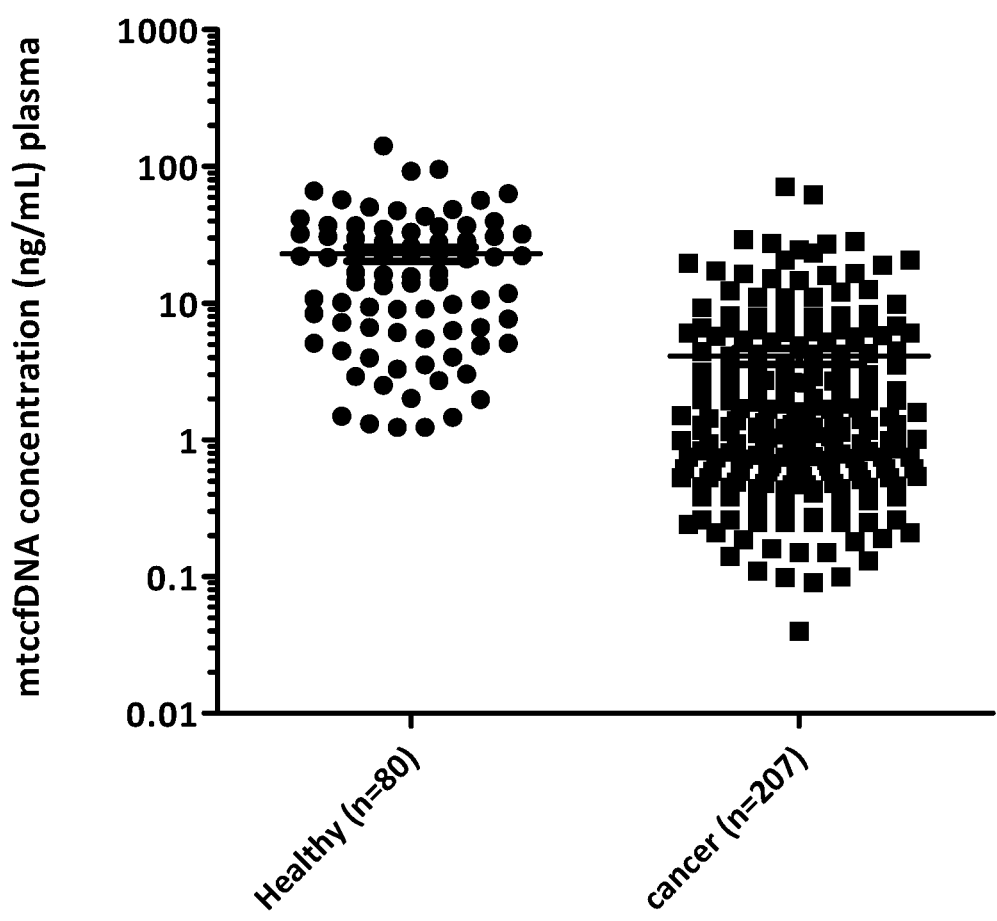

FIG. 7: Comparison between mitochondrial circulating DNA concentration in the blood of healthy individuals (n=80) and cancer patients (n=207).

Figure 8:
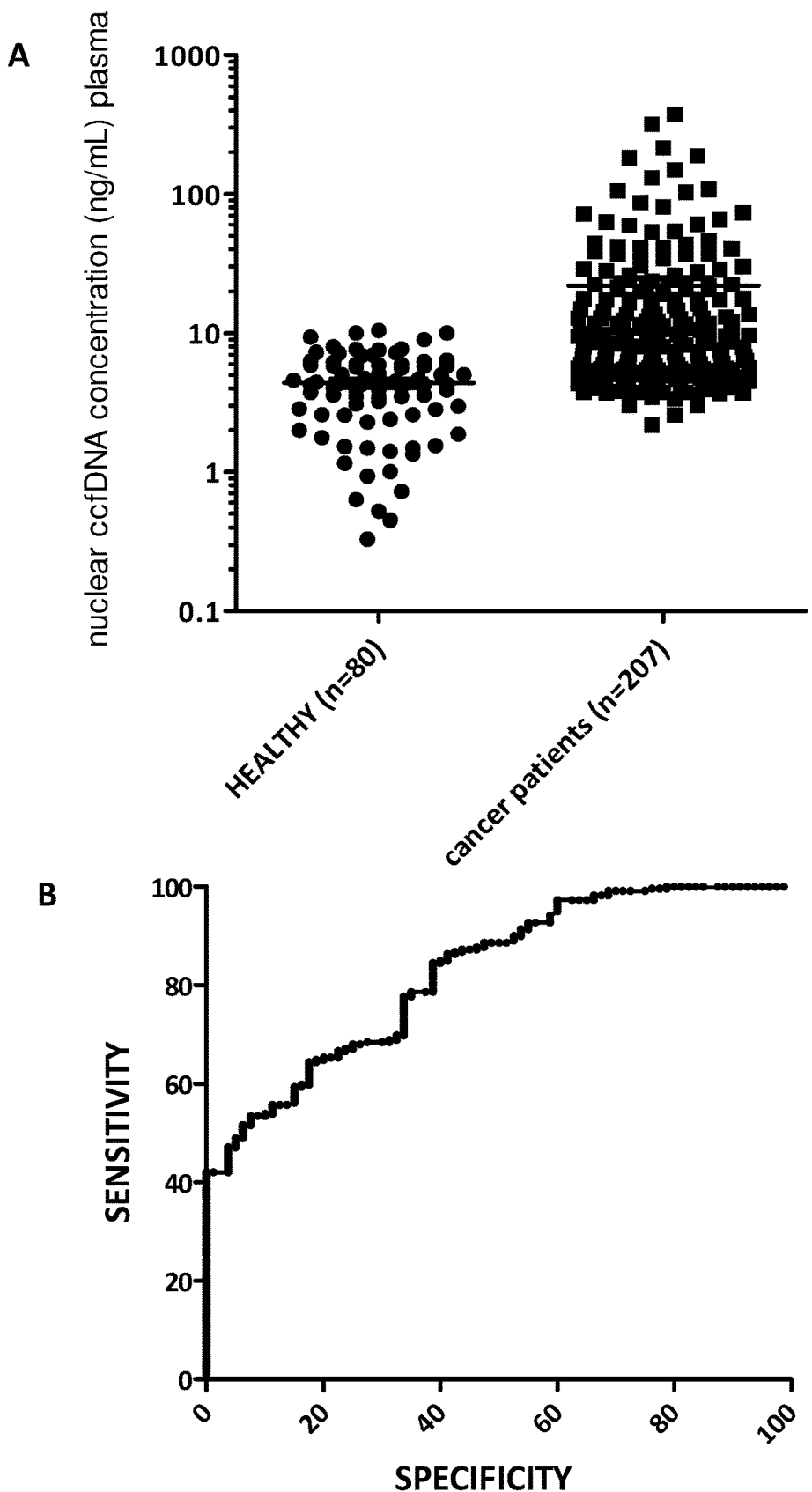

FIG. 8: A. Comparison between nuclear circulating DNA concentration in the blood of healthy individuals (n=80) and cancer patients (n=207). B. Diagnosis predictive capacity of nuclear ccfDNA concentration to distinguish plasma from cancer patients (n=207) and healthy subjects (n=80). ROC Curve representation deriving from the univariate logistic analysis corresponding to total ccfDNA (AUC=0.82).

Figure 9:
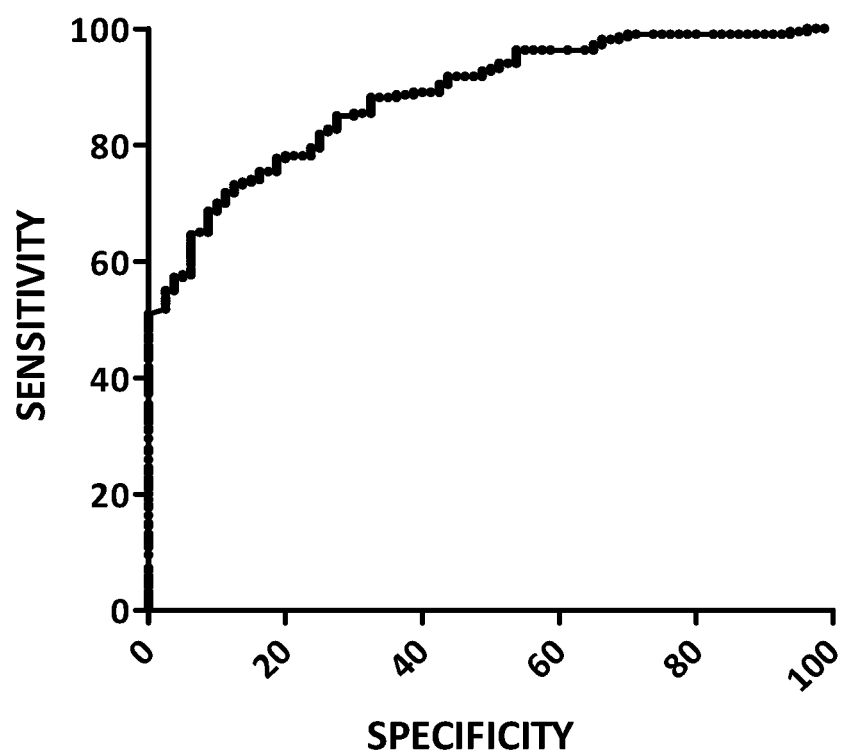

FIG. 9: ROC curve analysis of the CmDNA content with comparing 80 healthy and 207 cancer patients.

Figure 10:
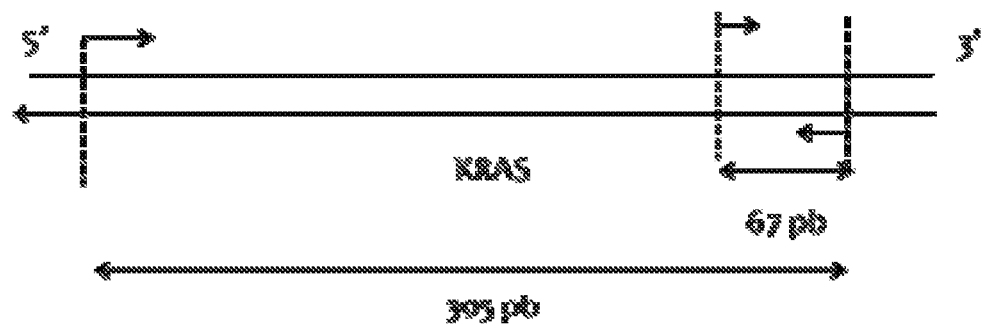
Figure 10:
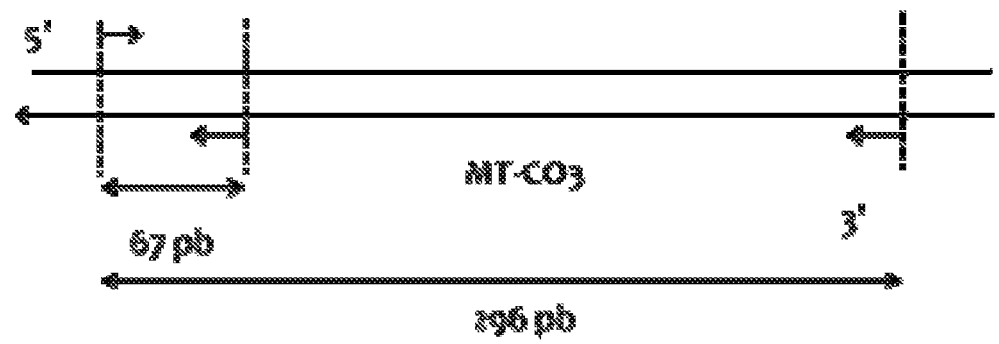

FIG. 10: Scheme of the design of the murine directed to mitochondrial and nuclear sequences detected in the Q-PCR assay.

Figure 11:
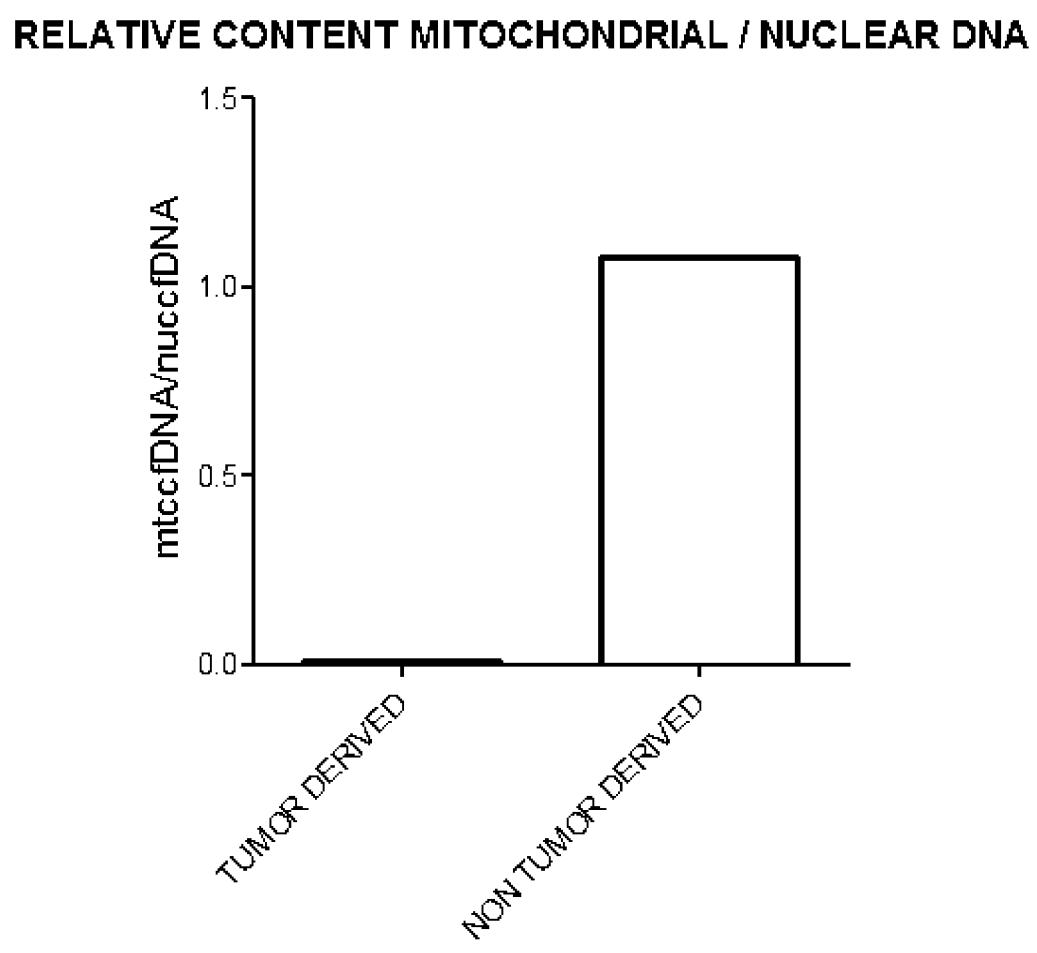

FIG. 11: Comparison of CmCnDNA content ratio from tumor and non-tumor derived ccfDNA in HCT 116 xenografted mice.

Figure 12:
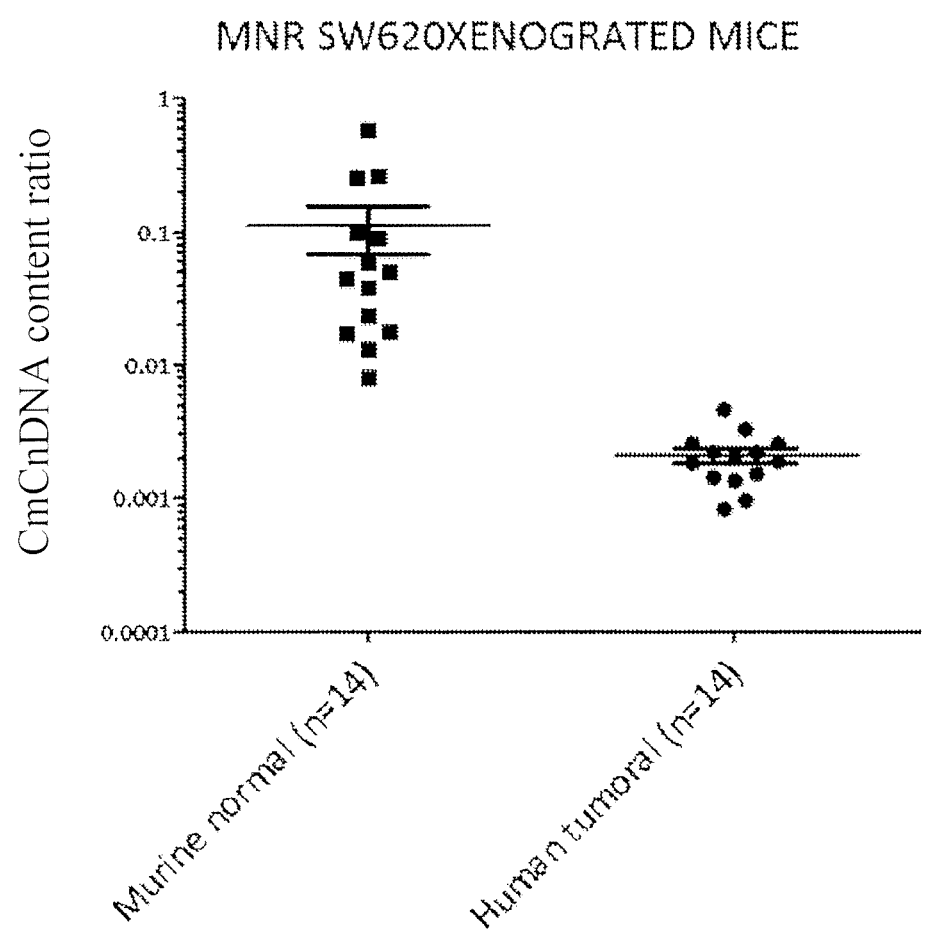

FIG. 12: Comparison of CmCnDNA content ratio from tumor and non-tumor derived ccfDNA in SW620 xenografted mice (n=14).

Figure 13:
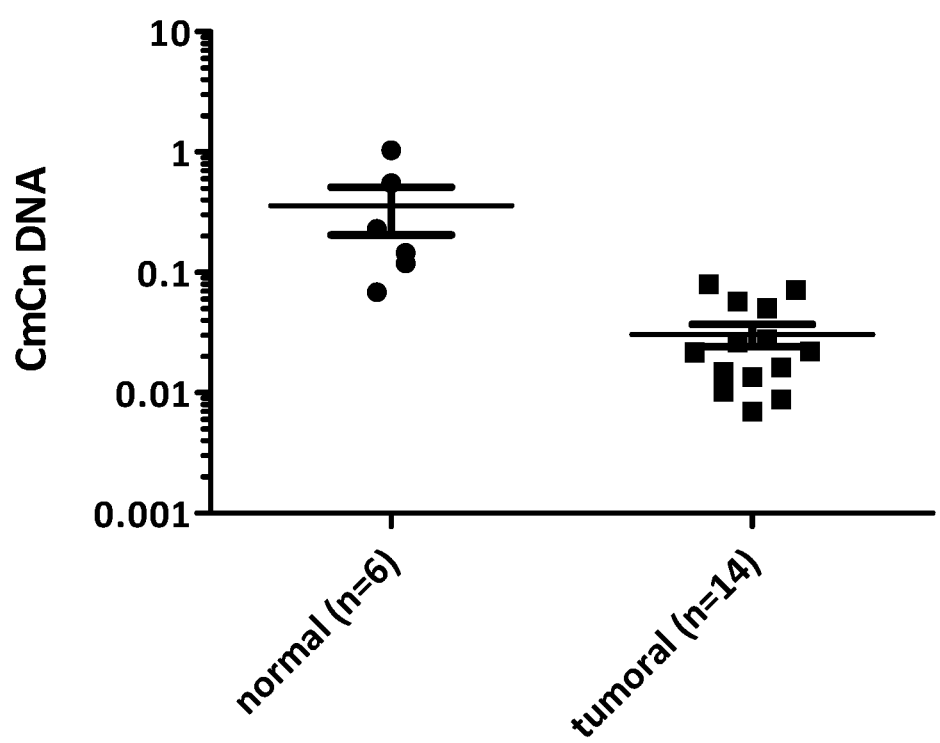

FIG. 13: Comparison between CmCnDNA content ratio in supernatant of various tumor cell lines and normal cell lines.

EXAMPLES

Example 1: Determination of CmCnDNA Content Ratio in Healthy and Cancer Individuals Material & Methods:

Blood samples from healthy individuals are obtained from the Etablissement français du sang (EFS convention no 21/PLER/MTP/INSERM02/2013-0073). Blood from CRC patients are obtained from the Kplex 1 and Kplex2 clinical study in which patients have signed an informed consent for genetic analysis from their blood. We also obtained blood samples from cohorts of hospital centers of Clermont-Ferrand and Limoges in France in which patients have signed an informed consent for genetic analysis from their blood. Lung cancer plasma samples come from Manchester Hospital (UK) in which patients have signed an informed consent for genetic analysis from their blood. HepatoCellular Cancer (HCC°) plasma samples were obtained from the CHU of Montpellier) in which patients have signed an informed consent for genetic analysis from their blood.

Plasma Isolation and ccfDNA Extraction:

Samples were handled according to the preanalytical guideline we established (CCA). A sample of 4 ml of blood was collected from patients in EDTA tubes. The blood was centrifuged at 1200 g at 4° C. in a Heraeus Multifuge LR centrifuge for 10 min. The supernatants were isolated in sterile 1.5 ml Eppendorf tubes and centrifuged at 16000 g at 4° C. for 10 min (Mouliere et al., 2011). Subsequently, the plasma was either immediately handled for DNA extraction or stored at −80° C. CcfDNA was extracted from 200 µL of plasma using the QIAmp DNA Mini Blood kit (Qiagen, Calif.) according to the "Blood and body fluid protocol" and our detailed protocol (Mouliere et al., 2013). DNA samples were kept at −20° C. until use.

Primer Design:

Primers were designed using the Primer 3 software and all sequences were checked for self- or intermolecular annealing with nucleic-acid-folding software (mfold and oligo-Analyzer 1.2). We performed local-alignment analyses with the BLAST program to confirm the specificity of the designed primers. Oligonucleotides were synthesized and purified on HPLC by Eurofins (Ebersberg, Germany) and quality control of the oligonucleotides was performed by MALDI TOF. The sequences and characteristics of the selected primers are presented in the Table 1 (SEQ ID NO:2; SEQ ID NO:3; SEQ ID NO:4; SEQ ID NO:5; SEQ ID NO:6; and SEQ ID NO:7).

TABLE 1

Characteristics of the selected primers to study nuclear and mitochondrial cell-free DNA.

| PRIMER NAME | SENS | SEQUENCE | Tm | % GC | AMPLICON SIZE |
|---|---|---|---|---|---|
| MITOCHONDRIAL DNA | | | | | |
| MIT MT-CO3 F | sense | GAC CCA CCA ATC ACA TGC | 56 | 55.60 | |
| MIT MT-CO3 R 67 | anti-sense | TGA GAG GGC CCC TGT TAG | 58.2 | 61.1 | 67 |
| MIT MT-CO3 R 296 | anti-sense | CTC AGA AAA ATC CTG CGA AGA | 55.9 | 42.9 | 296 |
| NUCLEAR DNA | | | | | |
| KRAS A1 inv | Sense | GCCTGCTGAAA ATGACTGA | 54.5 | | 305 |
| KRAS B1 inv | Sense | CCTTGGGTTTC AAGTTATATG | 54 | | 67 |
| KRAS B2 inv | Anti-sense | CCCTGACATAC TCCCAAGGA | 59.4 | | |

Genomic DNA and ccfDNA Quantification by Q-PCR:

Our Q-PCR experiments followed the MIQE guideline (Bustin et al., 2009). Q-PCR amplifications were carried out at least in duplicate in a 25 µl reaction volume on a CFX96 instrument using the CFX manager software (Bio-Rad). Each PCR reaction mixture was composed of 12.5 µl PCR mix (Bio-Rad Supermix So Advanced), 2.5 µl of each amplification primer (0.3 pmol/µl), 2.5 µl PCR-analyzed water, and 5 µl DNA extract. Thermal cycling consisted of three repeated steps: a 3-min. Hot-start Polymerase activation-denaturation step at 95° C., followed by 40 repeated cycles at 90° C. for 10 s, and then at 60° C. for 30 s. Melting curves were obtained by increasing the temperature from 55° C. to 105° C. with a plate reading every 0.2° C. The concentration was calculated from Cq detected by Q-PCR and also a control standard curve on DNA from Difi cell line of known concentration and copy number. Serial dilutions of genomic DNA from Difi cells were used as a standard for quantification and their concentration and quality was assessed using a Qubit spectrofluorimeter (Invitrogen). Cytochrome c oxidase subunit III (COIII or MTCO3) is 1 of 3 mitochondrial DNA (mtDNA) encoded subunits (MTCO1, MTCO2, MTCO3) of respiratory Complex IV, an enzyme of the electron transport chain of mitochondrial oxidative phosphorylation. As such it is purely specific to mitochondrial DNA.

Nuclear and Mitochondrial DNA Quantification and Fragmentation Study by Q-PCR:

Nuclear and Mitochondrial primer sets designs are represented in FIG. 1. For each DNA extract, short KRAS nuclear amplicon of 67 bp and short MT-CO3 mitochondrial amplicon of 67 bp were separately quantified. Each measure was reported to a standard curve realized with the same primer set. Each primer set present an efficacy near to 100%. Each measure was performed in triplicate.

To study relative ratio between mitochondrial and nuclear DNA, results from the quantitative PCR were expressed as the ratio of the mean mitochondrial DNA value of triplicate experiments to the mean nuclear DNA value of triplicate experiments (mDNA/nDNA). The same concentrations of genomic DNA were used for both 67 bp and 305 bp nuclear KRAS standard curves and for 67 bp and 296 bp mitochondrial MT-CO3 standard curve.

Figure 2C:
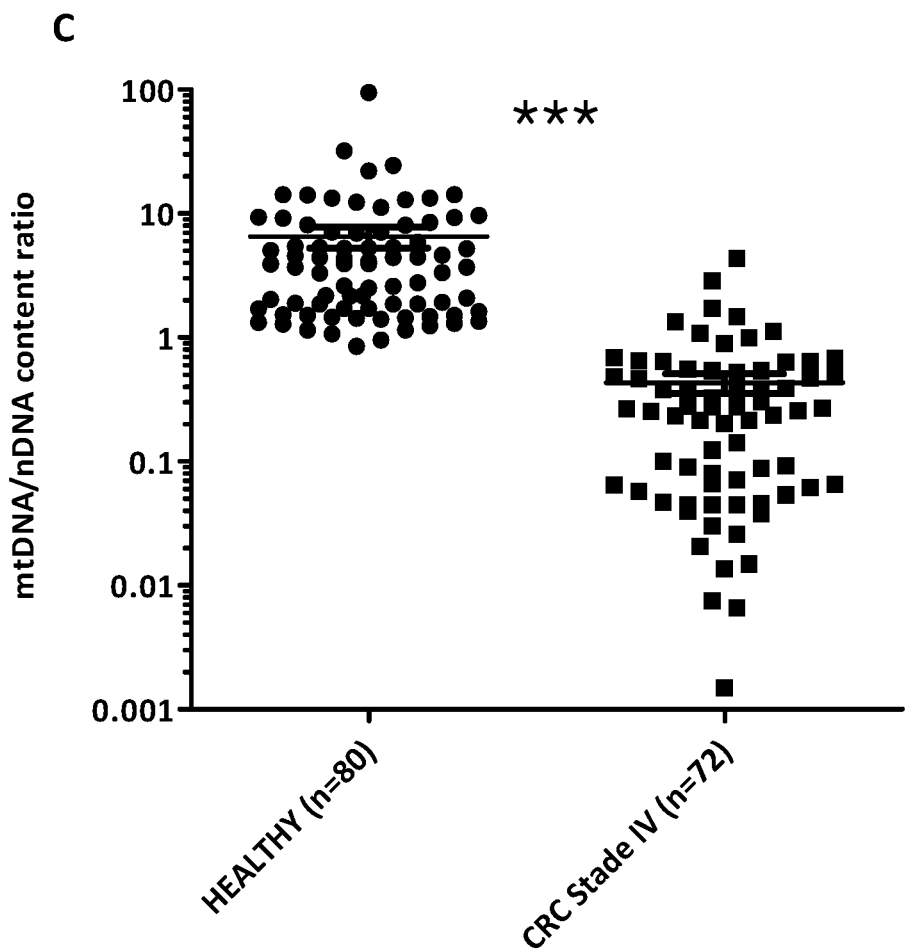

Results:

In order to compare the relative content of the mitochondrial ccfDNA vs the nuclear ccfDNA) data are expressed as the ratio of the concentration of mitochondrial ccfDNA to the concentration of nuclear ccfDNA (CmCnDNA content ratio) in 80 healthy and in 146 CRC individuals. Dot plot FIG. 2A shows a significant difference of relative content CmCnDNA content ratio between healthy and CRC samples. The median value of CmCnDNA in healthy subjects (3.8) was strongly significantly higher than that of CRC patients (0.18) (student t-test: $p<0.0001$). This observation is confirmed when separating stage IV patients (n=72) from stage I-III patients (n=74). There is a significant difference between Stage I-III CRC patients and healthy subjects when analyzing the CmCnDNA content ratio. Median value in stage I-III CRC patients was 0.17 while it was 3.8 in healthy subjects (student t-test $p<0.0001$) (FIG. 2B). In stage IV patients, median value was 0.25 and was significantly lower than in healthy subjects ($p<0.0001$) (FIG. 2C). This strong diagnosis capacity was illustrated the ROC curve analysis showing an AUC of 0.98 which is clearly optimal when comparing healthy subjects and CRC patients (FIG. 3 A, B, C). We also studied the CmCnDNA content ratio in a cohort of lung cancer patients (n=73). CmCnDNA content ratio was significantly higher in healthy donors (n=80) than in lung cancer patients. Median of CmCnDNA content ratio was 3.8 in healthy subjects while it was of 0.09 in lung cancer patients (student t-test $p<0.0001$) (FIG. 4). Those results confirmed the strong diagnostic capacity of CmCnDNA content ratio to discriminate healthy subjects and cancer patients (AUC Roc curve=0.99) (FIG. 5). As presenting in FIG. 6 there is no overlapping between values found in healthy and cancer patients. One would note that CmDNA content only exhibits a statistic significant diagnostic capacity but to a lesser extent than CmCnDNA content ratio since overlapping exist between values of Healthy and cancer patients (FIG. 7).

DNA base ratio in mtDNA resemble those of prokaryotic cells, and is more than those of nuclear DNA. mtDNA forms a loop from which replication begins and goes in one direction. Mitochondrial DNA contains more guanine-cytosine (GC) contents than nuclear DNA and is of higher density. As a result comparison between CmDNA and CnDNA can be performed in analyzing GC content or density. For instance, denaturation or melting temperature of mtDNA (and as a consequence cmDNA) is higher than the nuclear DNA.

Similarly, to mtDNA there are differences between mitochondrial RNA (mtRNA) and nucRNA. It is synthesized inside mitochondria on DNA template. It is different from RNA of nuclear origin as it is resistant to ribonuclease enzyme. As such level of resistance to ribonuclease of total ccfDNA content is a potential biomarker to screen for cancer, by use of reference standard.

This stricking results is of unmatched importance in regards to screen for cancer. Mitochondrial DNA appears non fragmented in comparison with nuclear DNA in the blood circulation. Explanation relies on three hypothesis: (1), there is less release of mDNA in the circulation in cancer cells; (2), there is more release of nDNA in the circulation in cancer cells; and (3), released mDNA is less stable than nDNA in blood. This would suggest that apoptosis is highly involved in cancer cells. No obvious morphological change of mitochondria are observed until the end stage of apoptosis (Ozawa T, Bioscience reports, 17, 337-250, 1997). DNA fragmentation during apoptosis appears as a specific nuclear event. Since mitochondria may release specific mitochondria apoptogenic proteins such as caspase or cytochrome C, it is possible that mitochondria and its DNA are preserved to preserve full process of the apoptosis. Since mDNA from apoptosis could be not degraded, apoptotic event is the biological phenomena involved in this difference found in cancer and healthy individuals. Certainly apoptosis event is highly occurring in cancer cells, such as CRC cancer.

Example 2: Combining CmCnDNA Content Ratio and Concentration of Total Circulating Nuclear DNA for Discriminating Healthy and Cancer Individuals Total concentration of nuclear circulating DNA (CnDNA concentration) in the same cohort of healthy individuals (n=80) and in cancer patients (n=207) was calculated and presented in FIG. 8A. There is a very strong statistic significant difference of CnDNA content in blood between healthy and cancer subjects (p<0.0001). Diagnosis predictive capacity of total ccfDNA concentration to distinguish plasmas from mCRC patients and healthy subjects is presented in FIG. 8B. The ROC Curve representation deriving from the univariate logistic analysis corresponding to total ccfDNA (FIG. 8B, AUC=0.82) confirm it while being slightly lower when using CmCnDNA content ratio. This observation was already made (CNRS Patent and Mouliere et al, Mol. Oncol). It is the subject of the invention to combine both analysis for its improving screen test power. Combination of both biomarker can be envisaged for instance by use of an algorythm. Note, correlation analysis between CmCnDNA content ratio content and CnDNA content is poor in healthy subjects (Spearman, p=0.64) and seems better in cancer patients (p=0.08) patients. Note there is lower diagnostic capacity when analysing only CmDNA as presented in FIG. 9.

Values of CmCnDNA content ratio in 3 hepatocellular cancer (HCC) patients was strongly significantly lower (0.004; 0.152 and 0.084; mean=0.080) than the median of healthy subjects (3.8) and do not overlap with values with values obtained from healthy subjects.

TABLE 2

Determination of the CmCn ratio from triplicate measurement of Cm and Cn in plasma of three patients with diagnosed HCC patients.

|  | Cm (ng/mL) | Cn (ng/mL) | CmCn ratio |
|---|---|---|---|
| patient 1 | 0.06 | 15.68 | |
| | 0.06 | 13.15 | |
| | 0.07 | 15.01 | |
| mean | 0.06 | 14.61 | 0.004 |
| patient 2 | 0.86 | 6.95 | |
| | 1.79 | 7.46 | |
| | 0.59 | 6.92 | |
| mean | 1.08 | 7.11 | 0.152 |
| patient 3 | 0.4 | 4.64 | |
| | 0.45 | 1.66 | |
| | 0.34 | 8.06 | |
| mean | 0.4 | 4.79 | 0.084 |

Data obtained from plasma of different types of cancer (CRC, HCC, Lung or breast cancers) show the potential of the determination of the CmCnDNA content ratio to discriminate healthy subjects and patients with all types of cancer.

Example 3: Determination of CmCnDNA DII Ratio in Healthy and Cancer Individuals Integrity can be evaluated by determining the DNA integrity index (DII) calculated as the ratio of the content of circulating DNA fragment over the content of circulating DNA fragment of a lower size. Typically we can use Q-PCR analysis: for each DNA extract long nuclear KRAS amplicon of 305 bp and long mitochondrial MT-CO3 amplicon of 296 bp were quantified in separate run. Nuclear and Mitochondrial DII were calculated by the ratio of the concentration determined with the primer set targeting a long sequence to the concentration determined with the primer set targeting a 67 bp region. DII of each samples of the both groups of individuals are shown in Table 3. Although diagnosis capacity is much lower than that of CmCnDNA content ratio, CmCnDNA DII ratio has diagnosis power which might be combined or associated with CmCnDNA content ratio.

TABLE 3

Diagnostic capacity of the CmCnDNA DII ratio. DII, DNA Integrity Index.
HEALTHY, healthy individuals. CRC, colorectal cancer patients.

|  | genomic DNA | Healthy 1 | Healthy 2 | Healthy 3 | CRC1 | CRC2 | CRC3 |
| --- | --- | --- | --- | --- | --- | --- | --- |
| DII NUC | 1.1308 | 0.2700 | 0.1468 | 0.0470 | 0.0985 | 0.0423 | 0.0192 |
| DII MITO | 1.1000 | 0.8715 | 1.4532 | 1.2500 | 0.8671 | 0.9680 | 1.0747 |
| DII MITO/DII NUC | 0.9727 | 3.2278 | 9.9007 | 26.5957 | 8.8021 | 22.9070 | 55.9084 |

Example 4: Experimental Demonstration in an Animal Model of the Interest in Using CmDNA for Distinguishing Tumor and Non-Tumor Origin In order to confirm our hypothesis we evaluated CmCnDNA content ratio in blood of an experimental mouse xenograft model previously designed (Thierry et al, NAR, 2010) allowing to distinguish in the same subject non-tumor derived ccfDNA (of murine origin) and tumor derived ccfDNA (of human origin). We studied our hypothesis on one HCT116 xenografted mouse and on 14 SW620 xenografted mice. Human CmCnDNA (tumor origin of cirDNA) and murine CmCnDNA (non-tumor origin of cirDNA) were determined in the same murine plasma samples using adequate primer sets for each amplification. Human CmCnDNA was calculated by the ratio between human mtccfDNA concentration to human nccfDNA concentration. Murine CmCnDNA was calculated by the ratio between murine mtccfDNA concentration to murine nccfDNA concentration.

Design of Q-PCR system and primer sequence are shown in FIG. 10. Table 4 presents the primers sequence directed to a mitochondrial and nuclear sequences detected in the Q-PCR assay (SEQ ID NO:8; SEQ ID NO:9; SEQ ID NO:10; SEQ ID NO:11; SEQ ID NO:12; and SEQ ID NO:13).

TABLE 4

Characteristics of the selected primers to study nuclear and mitochondrial cell-free DNA of murine origin

| PRIMER NAME | SENS | SEQUENCE | Tm | % GC | AMPLICON SIZE |
| --- | --- | --- | --- | --- | --- |
| MITOCHONDRIAL DNA | | | | | |
| MUMT $CO_1$ F | Sense | GTCCCACTAATA ATCGGAGC | 60 | 50 | |
| MUMT $C_{O1}$ REV C | Antisense | TGCTTCTACTAT TGATGATGC | 58 | 55.5 | 114 |
| MUMT $CO_1$ REV L | Antisense | TTGATACTGTGT TATGGCTG | 56 | 40 | 294 |
| NUCLEAR DNA | | | | | |
| KRAS 63-382 Mf | sense | AAGAGTGAAGAC CCGTGTGC | 59.4 | 55.00 | |
| KRAS 63 Mr | antisense | GGAGAACAAGCA CCCAACAG | 59.4 | 55 | 63 |
| KRAS 284 Mr | antisense | GTCTTTGTAATT CCCAACCTCCT | 58.9 | 43.5 | 284 |

Data are shown in FIGS. 11 and 12.

In the HCT116 xenografted mouse model, CmCnDNA content ratio of Tumor-derived ccfDNA is 0.007 while that of non tumor-derived ccfDNA is 1.08 (154-fold difference) suggesting that this biomarker is of high value for screening (FIG. 11). In the 14 SW620 xenografted mice, median value of murine CmCnDNA (0.047) was significantly higher than median value of human CmCnDNA (0.0020). (paired t-test p=0.023)(FIG. 12).

They may indicate that a strong difference of liberation in the circulation of mitochondrial DNA between tumor cells and non tumor cells, or a strong difference of their respective stability due to their structures and natures. Note, in the HCT116 xenografted model, the CmCnDNA DII ratio is much higher in tumor-derived ccfDNA (~20) than in non-tumor ccfDNA (~4).

Example 4: In Vitro Experimental Demonstration of the Interest in Using CmDNA for Distinguishing Cells from Tumor and Non-Tumor Origin As it has been shown that extracellular DNA is present in the supernatant of cell cultures, we evaluated CmCnDNA content ratio in the supernatant of cell cultures. We tested our hypothesis on extracellular DNA released by tumor cell lines and normal cell lines. We analyzed 14 tumor cell lines of various origins (5 prostate cell lines, 3 breast cancer cell lines, 3 CRC cell lines, 2 lymphoma cell lines, 1 lung cancer cell line) and 6 normal cell lines of various origins (human breast, foreskin, skin, lung, hepatocytes and murine embryo fibroblasts). Results are shown in table 5 and FIG. 13.

Median value of CmCnDNA content ratio was significantly higher in the supernatant from normal cell lines (0.20) than the median value of CmCnDNA content ratio in the supernatant from tumor cell lines (0.020) (student t-test, p=0.0011). They may confirm our other observations on clinical samples and murine experimental samples that there may be a strong difference of liberation in the circulation of mitochondrial DNA between tumor cells and non tumor cells.

TABLE 5

CmCnDNA content ratio in supernatant of various tumor cell lines and normal cell lines.

| | origin | identification | CmCnDNA content ratio |
| --- | --- | --- | --- |
| Tumor cell line | prostate | VCAP | 0.0573 |
| | | 22rV1 | 0.0088 |
| | | DU145 | 0.0102 |
| | | LNCAP | 0.0505 |
| | | PC3 | 0.0795 |
| | breast | MDA 468 | 0.0216 |
| | | R2shP53 | 0.0276 |
| | | SUM159 | 0.015 |

TABLE 5-continued

CmCnDNA content ratio in supernatant of various tumor cell lines and normal cell lines.

| origin | | identification | CmCnDNA content ratio |
|---|---|---|---|
| | colon | SW620 | 0.0135 |
| | | SW480 | 0.0161 |
| | | CaCo2 | 0.022 |
| | Lymphome B | Ramos | 0.007 |
| | Lymphome de burkitt | BJAB | 0.0262 |
| | Lung Cancer | H1975 | 0.0714 |
| Normal cell line | murine embryo fibroblasts | MEF | 0.2299 |
| | human mammary fibroblasts | R2 | 0.1447 |
| | human foreskin fibroblasts | HFF | 0.5517 |
| | human skin fibroblasts | CDC45K | 0.1191 |
| | human lung fibroblasts | IMR90 A | 0.0685 |
| | human normal hepatocytes | LWFD | 1.0341 |

As exemplified by the example 5 where supernatant of healthy cells showed to be in term of CmCn ratio statistically different as compared to cancer cell lines of various types (breast, colorectal, prostate, lung cancers and lymphoma), CmCn ratio appears useful to discriminate cfDNA from many cancer types either being solid tumours or liquid tumours. Therefore, it seems that analysis by calculating CmCn ratio enables to distinguish cfDNA deriving from normal cells from cfDNA from cancer cells, highlighting its capacity in cancer screening.

REFERENCES

Throughout this application, various references describe the state of the art to which this invention pertains. The disclosures of these references are hereby incorporated by reference into the present disclosure.

The invention claimed is:

1. A method for treating a subject having colorectal cancer comprising the steps of
   i) extracting cell free nucleic acids from a sample obtained from the subject,
   ii) determining a total concentration of mitochondrial cell free nucleic acids,
   iii) determining a total concentration of nuclear cell free nucleic acids,
   iv) calculating a ratio (CmCn content ratio) of the total concentration of mitochondrial cell free nucleic acids determined at step ii) to the total concentration of nuclear cell free nucleic acids determined at step iii),
   v) determining that the subject suffers from colorectal cancer when the ratio determined at step iv) is lower than 3.8, and
   vi) administering a colorectal anti-cancer treatment to the subject determined to suffer from colorectal cancer, wherein the colorectal anticancer treatment is at least one of radiotherapy, chemotherapy, immunotherapy, adjuvant therapy, or surgical resection.

2. The method of claim 1 wherein the cell free nucleic acids are cell free DNA nucleic acids (ccfDNA).

3. The method of claim 1 wherein the total concentration of cell free nucleic acids is determined by Q-PCR.

4. The method of claim 1 further comprising the steps of a) amplifying and quantifying a nuclear target nucleic acid sequence and b) amplifying and quantifying a mitochondrial target nucleic acid sequence.

5. The method of claim 4 wherein one or both of the nuclear target nucleic acid sequence and the mitochondrial target nucleic acid sequence is part of a coding or non-coding sequence.

6. The method of claim 4 wherein the mitochondrial target nucleic acid sequence is comprised in a mitochondrial gene selected from the group consisting of ND1; ND2; COX1; COX2; ATP8; ATP6; COX3; ND3; ND4L; ND4; ND5; ND6; CYTB; TRNF; TRND; RNR1 TRNV; TRNK; RNR2 TRNL1; TRNS1; TRNI; TRNP; TRNQ; TRNE; TRNM; TRNT TRNW; TRNL2 TRNA; TRNS2; TRNN; TRNR; TRNA; TRNG; TRNN; TRNC; and TRNY.

7. The method of claim 4 wherein the mitochondrial target nucleic acid sequence is comprised in a non-coding region of the mitochondrial genome.

8. The method of claim 4 wherein the mitochondrial target nucleic acid sequence and the target nuclear nucleic acid sequence have about the same length.

9. The method of claim 4 wherein the mitochondrial target nucleic acid sequence is 1; 2; 3; 4; 5; 6; 7; 8; 9; 10; 11; 12; 13; 14; or 15% longer or shorter than the nuclear target nucleic acid sequence.

10. The method of claim 4 wherein the mitochondrial and nuclear target nucleic acid sequences have the same length.

11. The method of claim 4 wherein the mitochondrial and nuclear target nucleic acid sequences have a length of less than 110 base pairs.

12. The method of claim 4 wherein the mitochondrial and nuclear target nucleic acid sequences have a length of 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; 100; 101; 102; 103; 104; 105; 106; 107; 108; 109; or 110 base pairs.

13. The method of claim 4, wherein 2 sets of 2 primers are used, and wherein one set of the 2 primers is used for amplifying the nuclear target nucleic acid sequence and one set of the 2 primers is used for amplifying the mitochondrial target nucleic acid sequence.

14. The method of claim 1 wherein the sample is a body fluid sample selected form the group consisting of blood, ascite, urine, amniotic fluid, feces, saliva and cerebrospinal fluids.

15. The method of claim 1 wherein the sample is a blood sample.

16. The method of claim 1 wherein the colorectal cancer is a metastatic colorectal cancer.

* * * * *